(12) United States Patent
Albrecht et al.

(10) Patent No.: US 7,125,995 B2
(45) Date of Patent: Oct. 24, 2006

(54) SUBSTITUTED AMIDOALKYL URACILS AND THEIR USE AS INHIBITORS OF THE POLY(ADP-RIBOSE) SYNTHETASE (PARS)

(75) Inventors: Barbara Albrecht, Wülfrath (DE); Michael Gerisch, Wuppertal (DE); Gabriele Handke-Ergüden, Wülfrath (DE); Axel Jensen, Velbert (DE); Thomas Krahn, Hagen (DE); Werner Nickl, Waldkirch (DE); Felix Oehme, Wuppertal (DE); Karl-Heinz Schlemmer, Wuppertal (DE); Henning Steinhagen, Sulzbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 218 days.

(21) Appl. No.: 10/416,622

(22) PCT Filed: Nov. 2, 2001

(86) PCT No.: PCT/EP01/12694

§ 371 (c)(1),
(2), (4) Date: Dec. 29, 2003

(87) PCT Pub. No.: WO02/40455

PCT Pub. Date: May 23, 2002

(65) Prior Publication Data

US 2005/0075347 A1 Apr. 7, 2005

(30) Foreign Application Priority Data

Nov. 14, 2000 (DE) ................. 100 56 312

(51) Int. Cl.
*C07D 239/70* (2006.01)
*C07D 493/04* (2006.01)
*C07D 495/04* (2006.01)
*A61K 31/517* (2006.01)
*A61P 9/10* (2006.01)

(52) U.S. Cl. ............ 544/278; 544/284; 544/285; 514/252.16; 514/260.1; 514/266.21; 514/266.3

(58) Field of Classification Search .......... 514/252.16, 514/260.1, 266.21, 266.3; 544/278, 284, 544/285
See application file for complete search history.

(56) References Cited

U.S. PATENT DOCUMENTS 5,426,186 A  6/1995  Shaw et al. ............ 544/250
5,859,014 A  1/1999  Bantle et al. ............ 514/255

FOREIGN PATENT DOCUMENTS

| DE | 1959705 | 6/1971 |
| DE | 2126148 | 12/1972 |
| DE | 2142317 | 3/1973 |
| EP | 1142881 | 10/2001 |
| JP | 03264579 | 11/1991 |
| WO | 9702254 | 1/1997 |
| WO | 0042025 | 7/2000 |

OTHER PUBLICATIONS

Steinhagen, Henning; Gerisch, Michael; Mittendorf, Joachim; Schlemmer, Karl-Heinz; Albrecht, Barbara, Bioorganic & Medicinal Chemistry Letters 12(21), 3187-3190 (English) 2002.*

West, Anthony R., Solid State Chemistry and its Applications, Wiley, New York, 1988, pp. 358 & 365.*

Peukert, Stefan, et al, Expert Opin. Ther. Patents, 2004, 14(110, 1531-1551.*

Larner, Andrew J., Expert. Opin. Ther. Patents 2002, 12(4), 481-487.*

Szabó et al., "Role of poly(ADP-ribose) Synthetase in Inflammation and Ischaemia-reperfusion." TIPS, 19, 287-298 (1998).

Zhang, et al. "Nitric Oxide Activation of Poly(ADP-Ribose) Synthetase in Neurotoxicity." Science, 263, 687-689 (1994).

Wallis, et al., Neuroprotection Against Nitric Oxide Injury with Inhibitors of ADP-ribosylation, NeuroReport, 5, 245-248 (1993).

Endres, et al., Ischemic Brain Injury Is Mediated by the Activation Of Poly (ADP-Ribose) Polymerase. J. Cereb. Blood Flow Metabol., 17, 1143-1151 (1997).

(Continued)

Primary Examiner—Thomas C. McKenzie

(57) ABSTRACT

This application relates to compounds of formula (I) below

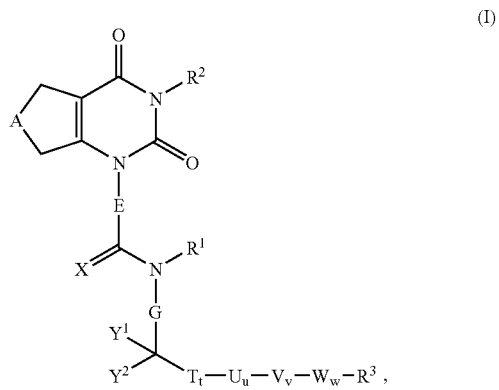

in which the several variable groups are as defined in the specification and claims, to methods of preparing these materials, to pharmaceutical compositions containing these materials, and to methods of using these materials to treat ischaemia or reperfusion damage.

11 Claims, No Drawings

OTHER PUBLICATIONS

Wallis et al., Traumatic Neuroprotection with Inhibitors of Nitric Oxide and ADP-ribosylation. Brain Res., 710, 169-177 (1996).

Thiemermann et al., "Inhibition of the Activity of Poly (ADP ribose) Synthetase Reduces Ischemia-Reperfusion Injury in the Heart and Skeletal Muscle", Proc. Nat. Acad. Sci., 94, 679-683 (1997).

Shimabukuro, et al., "Role of Nitric Oxide in Obesity-Induced $\beta$ Cell Disease". J. of Clin. Invest. 100, 290-295 (1997).

Zingarelli, et al., "Protective Effects of Nicotinamide against Nitric Oxide-Mediated Delayed Vascular Failure in Endotoxic Shock: Potential Involvement of polyADP Ribosyl Synthetase", SHOCK, 5, 258-264 (1996).

Weltin, et al, Effect of 6(5H)-Phenanthridinone, an Inhibitor of Poly(ADP-ribose) Polymerase, on Cultured Tumor Cells, Oncology Res. 6, 399-403 (1994).

Jijon et al., Inhibiton of poly(ADP-ribose)Polymerase Attenuates Inflammation in a Model of Chronic Colitis. Am. J. Physiol Gastrointest Liver Physiol. 279, G641-G651, (2000).

Tambuchi, et al., "Poly (Adenosine Diphosphate-Ribose) Synthetase Inhibitor 3-Aminobenzamide Alleviates Cochlear Dysfunction Induced by Transient Ischemia." Ann Otol Rhinol Laryngol, 110, 118-121, (2001).

Cuzzocrea, et al., "Protective Effects of 3-aminobenzamide, an Inhibitor of poly (ADP-ribose) synthase in a carrageenan-induced Model of local inflammation." Eur. J. of Pharma., 342 67-76, (1998).

Eriksson, et al., "3-Aminobenzamide: Effects On Cytochtome P450-Dependent Metabolism of Chemicals and on the Toxicity of Dichlobenil In the Olfactory Mucosa.", Toxic.and App. Pharma. 136, 324-331, (1996).

Watanabe, et al., "Syntheses of Monocyclic and Bicyclic 2,4(1$H$, 3$H$)-Pyrimidinediones and Their Serotonin 2 Antagonist Activities.", Chem. Pharm. Bull. 38, 2726-2732, (1990).

Basnak, I., "The Synthesis of some 5-Substituted and 5,6-Disubstituted 2'-Deoxyuridines.", Nucleosides & Nucleotides, 13(1-3), 177-196 (1994).

Renault, et al., Syntheseis and antiviral study of Cyclopentano [d] Pyrimidine-2,4-Diones and Octahydroquinazoline-2,4-Diones Acyclic Nucleosides and Potential Anti-Hiv Agents, Nucleosides & Nucleotides, 13(4), 891-901 (1994).

Rahim, et al., "Synthesis and Anti-Herpes Virus Activity of 2'-Deoxy-4'-Thiopyrimidine Nuceolsides," J. Med. Chem., 39, 89-795, (1996).

Peczak, et al., "Alkylated Derivatives of Uracil, Part X*, Synthesis of 2,4-Diketo-5,6,7,8-Tetrahydroquinazoline**," Pol. J. of Chem., 59, 317-326, (1985).

Draminski, et al., "Alkylated Derivatives of Uracil, Part IX*, Synthesis of N-(2,3-Dihydroxypropyl) Derivatives of 5,6-Tertramethyleneuracil, Structural Analogs of Nucleosides," Pol. J. Chem. 55, 1547-1552, (1981).

Szabo, et al., Protective Effect of an Inhibitor of Poly (ADF Ribora) Synthesis—Collagen-induced Arthritis, Japanese J. Pharm., 75, Supp 1:102 (1997).

\* cited by examiner

SUBSTITUTED AMIDOALKYL URACILS AND THEIR USE AS INHIBITORS OF THE POLY(ADP-RIBOSE) SYNTHETASE (PARS)

The present invention relates to novel chemical compounds, to a process for their preparation and to their use as medicaments, in particular for the prevention and/or therapy of ischaemia and reperfusion damage.

The elucidation of the molecular mechanism of cell death is the subject of intense biomedical research efforts. The aim is to find specifically active compounds which have modulating action in this process. When the individual biochemical steps resulting in cell death were examined, attention was drawn to poly(ADP-ribose)-synthetase (PARS), a protein which is expressed strongly in the cell nucleus and which is involved in deoxyribonucleic acid (DNA) damage repair [Szabo and Dawson, Trends in Pharmacological Sciences, 19, 287–298 (1998)].

Activation of PARS plays an important role in N-methyl-D-aspartate (NMDA)- and NO-induced neurotoxicity [Zhang et al., Science, 263, 687–689 (1994); Wallis et al., NeuroReport, 5, 245–248 (1993)], cerebral ischaemia [Endres et al., J. Cereb. Blood Flow Metabol., 17, 1143–1151 (1997)], traumatic brain injuries [Wallis et al., Brain Res., 710, 169–177 (1996)] and ischaemia/reperfusion damage to heart and skeletal muscle [Thiemermann et al., Proc. Nat. Acad. Sci., 94, 679–683 (1997)]. In addition, inhibition of PARS appears to have a positive effect on the therapy of arthritis [Szabo et al., Japanese J. Pharm., 75, Supp. 1:102 (1997)], diabetes [Shimabukuro et al., J. Clin. Invest., 100, 290–295 (1997)] and endotoxic or septic shock [Zingarelli et al., Shock, 5, 258–264 (1996)], radiosensitization of hypoxic tumour cells [Weltin et al., Oncol. Res., 6, 399–403 (1994)], chronic colitis [Jijon et al., Am. J. Physiol. Gastrointest. Liver Physiol., 279, G641–51 (2000)], sudden deafness [Tabuchi et al., Ann. Otol. Rhinol. Laryngol., 110(2), 118–21 (2001)], inflammatory pulmonary disorders, such as, for example, asthma and chronic bronchitis [Cuzzocrea et al., Eur. J. Pharm., 342, 67–76 (1998)] and cancer.

PARS, an enzyme which constructs polymeric ADP-ribose units from nicotinamide adenosine dinucleotide (NAD$^+$) as substrate, is activated when the DNA is damaged by single- or double-strand breaks. The polymeric ADP-ribose units formed are attached both to PARS itself and to other proteins, for example histones, topoisomerases and polymerases.

Increased activation of PARS results in a massive NAD$^+$ consumption. The strong decrease of the NAD$^+$ concentration and the resulting impediment of ATP synthesis (decrease of the ATP concentration) causes deterioration of the energetic state of the cell, which may lead to premature cell death (necrosis).

In the heart, reperfusion of ischaemic myocardium results in the generation of radicals, neutrophil infiltration, destruction of the myocardial tissue structure, contraction dysfunctions and necrosis. The $H_2O_2$ generated during the reperfusion phase reacts rapidly with NO, forming peroxynitrite. NO, peroxynitrite and $H_2O_2$ cause DNA strand breaks, thus resulting in overstimulation of PARS.

A further important point in the case of reperfusion damage is the accumulation of neutrophils in the reperfused myocardium. Activation of PARS increases the infiltration of neutrophils by stimulating the expression of P-selectin and ICAM-1.

Healthy PARS knock-out mice capable of reproduction are substantially protected against reperfusion damage. Infiltration of neutrophils is reduced by 50% and the structure of the myocardial tissue remains intact during the reperfusion phase.

In cases of ischaemia and reperfusion damage to heart and brain, low-molecular-weight PARS inhibitors, such as, for example, 3-aminobenzamide and 1,5-dihydroxyisoquinoline, protect the tissue against necrotic cell death (reduction of the infarct size by 30 to 48%) and delay myocardial and neuronal dysfunction.

However, the PARS inhibitors hitherto tested in animal experiments have various disadvantages. Thus, for example, 3-aminobenzamide is an unspecific PARS inhibitor which also inhibits cytochrome $P_{450}$ (Eriksson et al., Toxicology and applied Pharmacology, 136, 324–331 (1996)); in contrast, 5-iodo-6-amino-1,2-benzopyrone has serious side-effects (Szabo and Dawson, Trends in Pharmacol. Sciences, 19, 287–298 (1998)). Moreover, most inhibitors are not very potent and are therefore only efficacious in animals at a relatively high dosage (Thiemermann et al., Proc. Natl. Acad. Sci., 94, 679–683 (1997)).

JP-A-032645679 and Chem. Pharm. Bull. 38 (10), 2726–2732 (1990) disclose bicyclic 2,4-(1H,3H)-pyrimidinediones as 5-HT$_2$ antagonists for the treatment of cardiovascular diseases, depression and other mental disorders. U.S. Pat. No. 5,859,014 discloses tetrahydroquinazolinedione derivatives as $\alpha_1$ adrenergic receptor antagonists for the treatment of prostate hypertrophy. WO-A-00/42025 describes dihydropyrimidinones as PARS inhibitors. DE-A-1959705 and DE-A-2126148 list uracil derivatives for preparing crop protection agents. DE-A-2142317 mentions uracil derivatives having hypnotic properties. Furthermore, various bridged uracils are described in the literature as nucleoside analogues with potential antiviral action (for example Nucleosides Nucleotides 13 (1–3), 177–196; 13 (4), 891–902 (1994) and J. Med. Chem. 39 (3), 789–795 (1996)).

Accordingly, it is an object of the present invention to provide novel substances for the prevention and/or therapy of disorders, in particular of ischaemia and reperfusion damage.

Here, the compounds according to the invention presumably act as inhibitors of poly(ADP-ribose)-synthetase (PARS).

The present invention relates to compounds of the formula (I)

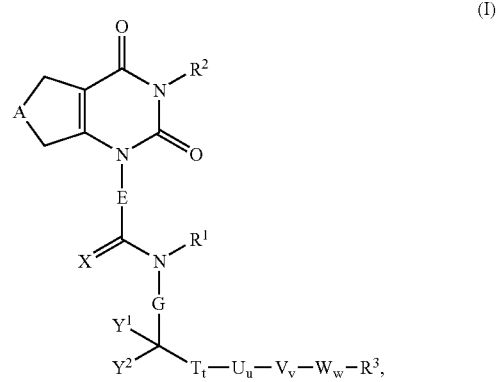

in which

A is a ring member selected from the group consisting of:
-D-,

—CH$_2$-D-,
-D-CH$_2$—,
—CH=CH—CH$_2$—,
—CH$_2$—CH=CH—,
—CH$_2$—CH$_2$-D-,
-D-CH$_2$—CH$_2$ and
—CH$_2$-D-CH$_2$—,
in which
D represents —CH$_2$—, —O— or —S—,
E represents (C$_1$–C$_6$)-alkylene or (C$_3$–C$_8$)-cycloalkylene which are optionally mono- or polysubstituted, independently of one another, by substituents selected from the group consisting of (C$_1$–C$_4$)-alkoxy, hydroxyl and amino,
G represents (C$_1$–C$_6$)-alkylene or (C$_3$–C$_8$)-cycloalkylene which are optionally mono- or polysubstituted, independently of one another, by substituents selected from the group consisting of (C$_1$–C$_4$)-alkoxy, hydroxyl and amino,
T represents a methylene group,
t represents 0 or 1,
U represents (C$_6$–C$_{10}$)-arylene, 5- to 7-membered heterocyclene having up to three heteroatoms from the group consisting of N, O and S or represents ethinediyl, where the ring systems may be substituted up to three times, independently of one another, by substituents selected from the group consisting of nitro, cyano, halogen, (C$_1$–C$_6$)-alkyl, (C$_3$–C$_8$)-cycloalkyl, (C$_1$–C$_6$)-alkoxy, trifluoromethyl, di- and trifluoromethoxy, hydroxyl, amino, mono- and di-(C$_1$–C$_6$)-alkylamino, (C$_1$–C$_6$)-alkoxycarbonyl, aminosulphonyl, (C$_1$–C$_6$)-alkylsulphonyl, mono- and di-(C$_1$–C$_6$)-alkylaminosulphonyl and (C$_1$–C$_6$)-alkanoyloxy,
u represents 0 or 1,
V represents (C$_6$–C$_{10}$)-arylene, 5- to 7-membered heterocyclene having up to three heteroatoms from the group consisting of N, O and S or represents ethinediyl, where the ring systems may be substituted up to three times, independently of one another, by substituents selected from the group consisting of nitro, cyano, halogen, (C$_1$–C$_6$)-alkyl, (C$_3$–C$_8$)-cycloalkyl, (C$_1$–C$_6$)-alkoxy, trifluoromethyl, di- and trifluoromethoxy, hydroxyl, amino, mono- and di-(C$_1$–C$_6$)-alkylamino, (C$_1$–C$_6$)-alkoxycarbonyl, aminosulphonyl, (C$_1$–C$_6$)-alkylsulphonyl, mono- and di-(C$_1$–C$_6$)-alkylaminosulphonyl and (C$_1$–C$_6$)-alkanoyloxy,
v represents 0 or 1,
W represents —O—, —S—, —CO—O—, —o—C— or —NR$^4$—.
in which
R$^4$ represents hydrogen or (C$_1$–C$_6$)-alkyl,
w represents 0 or 1,
x represents O, S or N—R$^5$,
in which
R$^5$ represents hydrogen, (C$_1$–C$_6$)-alkyl or benzyl,
Y$^1$ represents hydrogen,
Y$^2$ represents hydroxyl,
or
Y$^1$ and Y$^2$ together represent O, S or N—R$^6$,
in which
R$^6$ represents hydrogen, (C$_1$–C$_6$)-alkyl or benzyl,
R$^1$ represents hydrogen, (C$_1$–C$_6$)-alkyl which may be mono- or polysubstituted by halogen, or represents (C$_3$–C$_8$)-cycloalkyl,
R$^2$ represents hydrogen or (C$_1$–C$_6$)-alkoxycarbonyl,
and
R$^3$ represents (C$_6$–C$_{10}$)-aryl or a 5- to 13-membered heterocycle having up to four heteroatoms from the group consisting of N, O and S, where the ring systems may be substituted up to three times, independently of one another, by substituents selected from the group consisting of nitro, cyano, halogen, (C$_1$–C$_6$)-alkyl, (C$_3$–C$_8$)-cycloalkyl, (C$_1$–C$_6$)-alkoxy, trifluoromethyl, di- and trifluoromethoxy, hydroxyl, oxo, amino, mono- and di-(C$_1$–C$_6$)-alkylamino, mono- and di-(C$_1$–C$_6$)-alkylaminomethyl, (C$_1$–C$_6$)-alkoxycarbonyl, aminosulphonyl, (C$_1$–C$_6$)-alkylsulphonyl, mono- and di-(C$_1$–C$_6$)-alkylaminosulphonyl, (C$_1$–C$_6$)-alkanoyl, (C$_1$–C$_6$)-alkanoyloxy and —CH$_2$—R$^7$,
in which
R$^7$ represents a 5- to 7-membered heterocycle having up to three heteroatoms from the group consisting of N, O and S, and their salts, hydrates, hydrates of the salts and solvates.

Depending on the substitution pattern, the compounds of the formula (I) according to the invention can exist in stereoisomeric forms which are either like image and mirror image (enantiomers) or are not like image and mirror image (diastereomers). The invention relates both to the enantiomers or diastereomers and to their respective mixtures. The racemic forms, like the diastereomoers, can be separated in a known manner into the stereoisomerically uniform components.

Furthermore, certain compounds of the formula (I) can be present in tautomeric forms. This is known to the person skilled in the art, and such compounds are likewise included in the scope of the invention.

Moreover, the invention also embraces prodrugs of the compounds according to the invention. According to the invention, "prodrugs" are forms of the compounds of the formula (I) which for their part can be biologically active or inactive, but which can be converted under physiological conditions (for example metabolically or solvolytically) into the corresponding biologically active form.

"Salts" of the compounds according to the invention are physiologically acceptable salts of the substances according to the invention with mineral acids, carboxylic acids or sulphonic acids. Particular preference is given, for example, to salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts can also be physiologically acceptable metal or ammonium salts of the compounds according to the invention. Particular preference is given to alkali metal salts (for example sodium salts or potassium salts), alkaline earth metal salts (for example magnesium salts or calcium salts), and also to ammonium salts derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

According to the invention, "hydrates" or "solvates" are forms of the compounds of the formula (I) which, in the solid or liquid state, form a molecular compound or a complex by hydration with water or co-ordination with solvent molecules. Examples of hydrates are sesquihydrates, monohydrates, dihydrates or trihydrates. Likewise suitable are the hydrates and/or solvates of salts of the compounds according to the invention.

Halogen represents fluorine, chlorine, bromine and iodine. Preference is given to chlorine and fluorine.

($C_1$–$C_6$)-Alkyl represents a straight-chain or branched alkyl radical having 1 to 6 carbon atoms. Examples which may be mentioned are: methyl, ethyl, n-propyl, isopropyl, n-butyl, isobutyl, tert-butyl, n-pentyl and n-hexyl. The corresponding alkyl groups having fewer carbon atoms, such as, for example, ($C_1$–$C_4$)-alkyl and ($C_1$–$C_3$)-alkyl, are derived analogously from this definition. In general, ($C_1$–$C_3$)-alkyl is preferred.

Also derived from this definition is the meaning of the corresponding component of other more complex substituents, such as, for example, in the case of alkylene, in which an alkyl radical defined as above is attached via two positions, alkylsulphonyl, mono- and di-alkylaminosulphonyl, mono- and di-alkylamino or mono- and di-alkylaminomethyl.

Mono- or di-($C_1$–$C_6$)-alkylaminocarbonyl represents an amino group which is attached via a carbonyl group and has one or two identical or different straight-chain or branched alkyl substituents having in each case 1 to 6 carbon atoms. The corresponding mono- or di-alkylaminocarbonyl groups having fewer carbon atoms, such as, for example, mono- or di-($C_1$–$C_4$)-alkylaminocarbonyl, which are preferred, are derived analogously from this definition. Examples which may be mentioned are: methylarninocarbonyl, ethylaminocarbonyl, n-propylaminocarbonyl, isopropyl-aminocarbonyl, t-butylaminocarbonyl, N,N-dimethylaminocarbonyl, N,N-diethyl-aminocarbonyl, N-ethyl-N-methylaminocarbonyl, N-methyl-N-n-propylamino-carbonyl, N-isopropyl-N-n-propylaminocarbonyl and N-t-butyl-N-methylamino-carbonyl.

($C_1$–$C_8$)-Cycloalkyl represents a cyclic alkyl radical having 3 to 8 carbon atoms. Examples which may be mentioned are: cyclopropyl, cyclobutyl, cyclopentyl, cyclohexyl, cycloheptyl or cyclooctyl. The corresponding cycloalkyl groups having fewer carbon atoms, such as, for example, ($C_3$–$C_6$)-cycloalkyl, are derived analogously from this definition. Preference is given to cyclopropyl, cyclopentyl and cyclohexyl.

The meaning of the corresponding component of other more complex substitutents, such as, for example, in the case of cycloalkylene, in which a cyclo alkyl radical as defined above is attached via two positions, is also derived from this definition.

($C_1$–$C_6$)-Alkoxy represents a straight-chain or branched alkoxy radical having 1 to 6 carbon atoms. Examples which may be mentioned are: methoxy, ethoxy, n-propoxy, isopropoxy, n-butoxy, isobutoxy, tert-butoxy, n-pentoxy and n-hexoxy. The corresponding alkoxy groups having fewer carbon atoms, such as, for example, ($C_1$–$C_4$)-alkoxy and ($C_1$–$C_3$)-alkoxy, are derived analogously from this definition. In general, ($C_1$–$C_3$)-alkoxy is preferred.

The meaning of the corresponding component of other more complex substitutents, such as, for example, alkoxycarbonyl, in which an alkoxy radical as defined above is attached via a carbonyl group is also derived from this definition.

($C_1$–$C_6$)-Alkanoyl represents a straight-chain or branched alkyl radical having 1 to 6 carbon atoms which carries a doubly attached oxygen atom in the 1-position and is attached via the 1-position. Examples which may be mentioned are: formyl, acetyl, propionyl, n-butyryl, i-butyryl, pivaloyl and n-hexanoyl. The corresponding alkanoyl groups having fewer carbon atoms, such as, for example, ($C_1$–$C_4$)-alkanoyl, are derived analogously from this definition. In general, preference is given to ($C_1$–$C_4$)-alkanoyl.

($C_1$–$C_6$)-Alkanoyloxy represents a straight-chain or branched alkyl radical having 1 to 6 carbon atoms which carries a doubly attached oxygen atom in the 1-position and is attached via a further oxygen atom in the 1-position. Examples which may be mentioned are: acetoxy, propionoxy, n-butyroxy, i-butyroxy, pivaloyloxy and n-hexanoyloxy.

($C_6$–$C_{10}$)-Aryl represents an aromatic radical having 6 to 10 carbon atoms. Examples which may be mentioned are: phenyl and naphthyl.

The meaning of the corresponding component of other more complex substituents, such as, for example, arylene, in which an aryl radical as defined above is attached via two positions, is also derived from this definition.

A 5- to 13-membered heterocycle having up to 4 heteroatoms from the group consisting of N, O and S represents a mono- or bicyclic saturated, partially unsaturated or aromatic heterocycle which is attached via a ring carbon atom or a ring nitrogen atom. Examples which may be mentioned are: thienyl, furyl, pyridyl, pyrimidinyl, 1,2,3,4-tetrahydroquinolyl, 1,2,3,4-tetrahydroisoquinolyl, quinolinyl, isoquinolinyl, pyrazinyl, pyridazinyl, triazinyl, tetrazinyl, imidazopyridinyl, isoxazolyl, imidazolyl, pyrazolyl, oxazolyl, thiazolyl, triazolyl, tetrazolyl, thienopyrimidinyl, dihydroindolinyl, indolinyl, 1,3-benzodioxolyl, pyrrolidinyl, tetrahydrofuryl, pyrrolinyl, piperidinyl, piperazinyl, morpholinyl, azepinyl, 1,4-diazepinyl.

The corresponding heterocycles having a different ring size, such as, for example, 5- to 10-membered, 5- to 7-membered or 6-membered heterocycles, are derived analogously from this definition.

The meaning of the corresponding component of other more complex substituents, such as, for example, heterocyclene, in which a heterocyclyl radical as defined above is attached via two positions, is also derived from this definition.

Preference is given to compounds of the formula (I) according to the invention in which A represents a ring member —$CH_2$-D- or -D-$CH_2$—, in which D represents —$CH_2$—, —O— or —S—, E represents ($C_1$–$C_6$)-alkylene which is optionally mono- or polysubstituted, independently of one another, by substituents selected from the group consisting of ($C_1$–$C_4$)-alkoxy, hydroxyl and amino, G represents ($C_1$–$C_6$)-alkylene which is optionally mono- or polysubstituted, independently of one another, by substituents selected from the group consisting of ($C_1$–$C_4$)-alkoxy, hydroxyl and amino, t represents 0, U represents phenylene, 6-membered heterocyclene having up to three heteroatoms from the group consisting of N, O and S, where the ring systems may be substituted up to three times, independently of one another, by substituents selected from the group consisting of nitro, cyano, fluorine, chlorine, ($C_1$–$C_6$)-alkyl, ($C_3$–$C_6$)-cycloalkyl, ($C_1$–$C_6$)-alkoxy, trifluoromethyl, di- and trifluoromethoxy, u represents 0 or 1, V represents phenylene, 6-membered heterocyclene having up to three heteroatoms from the group consisting of N, O and S, where the ring systems may be substituted up to three times, independently of one another, by substituents selected from the group consisting of nitro, cyano, fluorine, chlorine, ($C_1$–$C_6$)-alkyl, ($C_3$–$C_6$)-cycloalkyl, ($C_1$–$C_6$)-alkoxy, trifluoromethyl, di- and trifluoromethoxy, v represents 0 or 1, W represents —O—, —S—, —CO—O—, —O—CO— or —$NR^4$—, in which $R^4$ represents hydrogen or ($C_1$–$C_6$)-alkyl, w represents 0 or 1,
X represents O,
$Y^1$ represents hydrogen,
$Y^2$ represents hydroxyl,
or
$Y^1$ and $Y^2$ together represent O,
$R^1$ represents hydrogen or $(C_1–C_6)$-alkyl which may be mono- or polysubstituted by halogen,
$R^2$ represents hydrogen,
and
$R^3$ represents phenyl, naphthyl or a 5- to 10-membered heterocycle having up to four heteroatoms from the group consisting of N, O and S, where the ring systems may be substituted up to three times, independently of one another, by substituents selected from the group consisting of nitro, cyano, halogen, $(C_1–C_6)$-alkyl, $(C_3–C_6)$-cycloalkyl, $(C_1–C_6)$-alkoxy, trifluoromethyl, di- and trifluoromethoxy, hydroxyl, oxo, amino, mono- and di-$(C_1–C_6)$-alkylamino, and their salts, hydrates, hydrates of the salts and solvates.

Particular preference is given to compounds of the formula (I) according to the invention in which
A represents a ring member —$CH_2$-D- or -D-$CH_2$—,
  in which
  D represents —$CH_2$— or —S—,
E represents a methylene or 1,2-ethylene group,
G represents a methylene or 1,2-ethylene group,
t represents 0,
U represents phenylene, pyridinediyl or piperazine-1,4-diyl,
u represents 0 or 1,
V represents pyrimidinyl,
v represents 0 or 1,
W represents —O—, —CO—O— or —O—CO—,
w represents 0 or 1,
X represents O,
$Y^1$ and $Y^2$ together represent O,
$R^1$ represents hydrogen,
$R^2$ represents hydrogen,
and
$R^3$ represents phenyl, naphthyl, thienyl, pyridyl, pyrazinyl, pyrimidinyl, thienopyrimidinyl, isoxazolyl, 1,3-benzodioxolyl or pyrrolidinyl, where the ring systems may in each case be substituted up to two times, independently of one another, by substituents selected from the group consisting of nitro, cyano, bromine, chlorine, fluorine, hydroxyl, $(C_1–C_3)$-alkoxy, $(C_1–C_3)$-alkyl, $(C_3–C_6)$-cycloalkyl, trifluoromethyl, amino and di-$(C_1–C_3)$-alkylamino, and their salts, hydrates, hydrates of the salts and solvates.

Very particular preference is given to the compounds of Examples 4, 5, 7, 15, 16, 19, 23, 31 and 138 and their salts, hydrates, hydrates of the salts and solvates.

The present invention also provides a process for preparing the compounds of the formula (I) according to the invention, where compounds of the formula (II)

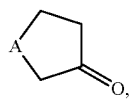

(II)

in which
A is as defined above are reacted with compounds of the formula (III)

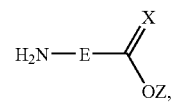

(III)

in which
Z represents an alkyl or benzyl radical and E and X are each as defined above to give compounds of the formula (IV)

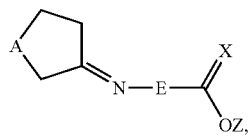

(IV)

in which
Z represents an alkyl or benzyl radical and A, E and X are each as defined above, the product is then reacted with chlorocarbonyl isocyanate to give compounds of the formula (V)

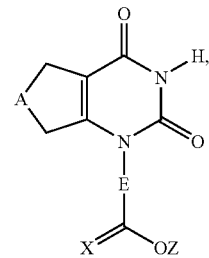

(V)

in which
Z represents an alkyl or benzyl radical and A, E and X are as defined above, the resulting reaction product is, in a subsequent step, converted into the compounds of the formula (VI),

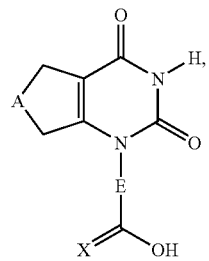

(VI)

in which

A, E and X are each as defined above, which is, if appropriate, activated, in particular by conversion into a suitable carboxylic acid derivative, such as, for example, a carbonyl halide, a carboxylic anhydride, a carboxamide or a carboxylic ester, and then either

[A] converted using compounds of the formula (VII)

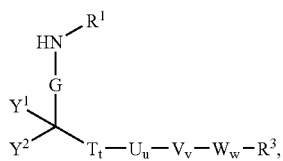 (VII)

in which G, $R^1$, $R^3$, T, U, V, W, $Y^1$, $Y^2$, t, u, V and w are each as defined above, and which are, if appropriate, used in the form of their salts, and compounds of the formula (VIII)

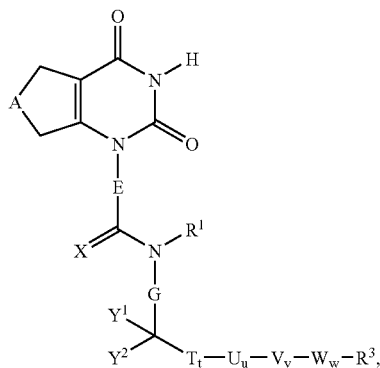 (VIII)

in which A, E, G, $R^1$, $R^3$, T, U, V, W, X, $Y^1$, $Y^2$, t, u, v and w are as defined above, or

[B] converted using compounds of the formula (VIIa),

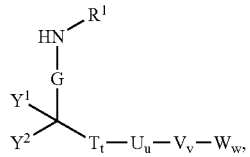 (VIIa)

in which G, $R^1$, T, U, V, $Y^1$, $Y^2$, t and u are as defined above, v is 1, w is 0 and V contains as an additional substituent a suitable leaving group, such as halogen, preferably bromine or iodine, or triflate, and which are, if appropriate, used in the form of their salts, via the stage of compounds of the formula (VIIIa),

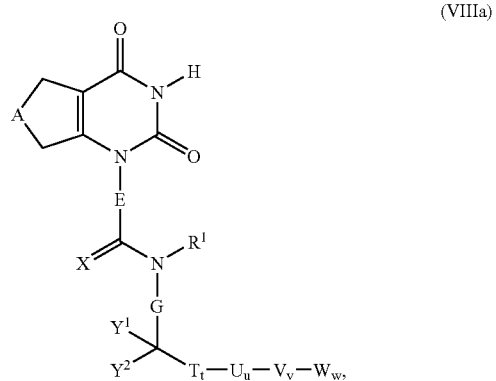 (VIIIa)

in which A, E, G, $R^1$, T, U, V, X, $Y^1$, $Y^2$, t and u are as defined above, v is 1, w is 0 and V contains as an additional substituent a suitable leaving group, such as halogen, preferably bromine or iodine, or triflate, and a subsequent aryl coupling reaction in the presence of a catalyst with compounds of the formula (IX)

$R^3$-M (IX)

in which $R^3$ is as defined above and M is an optionally substituted metallic or semimetallic element, such as, for example, zinc, magnesium, boron, lithium, copper or tin, into compounds of the formula (VIII)

and compounds of the formula (VIII) are, if appropriate, reacted with compounds of the formula (X)

$R^2$-Q (X)

in which $R^2$ is as defined above, but not hydrogen, and Q represents a leaving group, to give compounds of the formula (I) in which $R^2$ is not hydrogen.

If appropriate, the compounds of the formula (I) obtained in this manner can then be converted into the corresponding salts, for example by reaction with an acid.

The process according to the invention for preparing compounds of the formula (I) can be illustrated in an exemplary manner by the equations below:

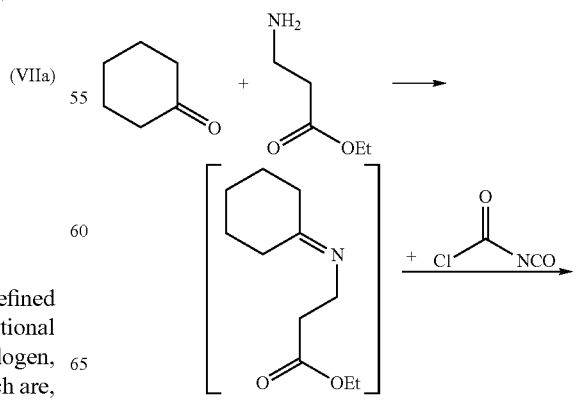

11
-continued
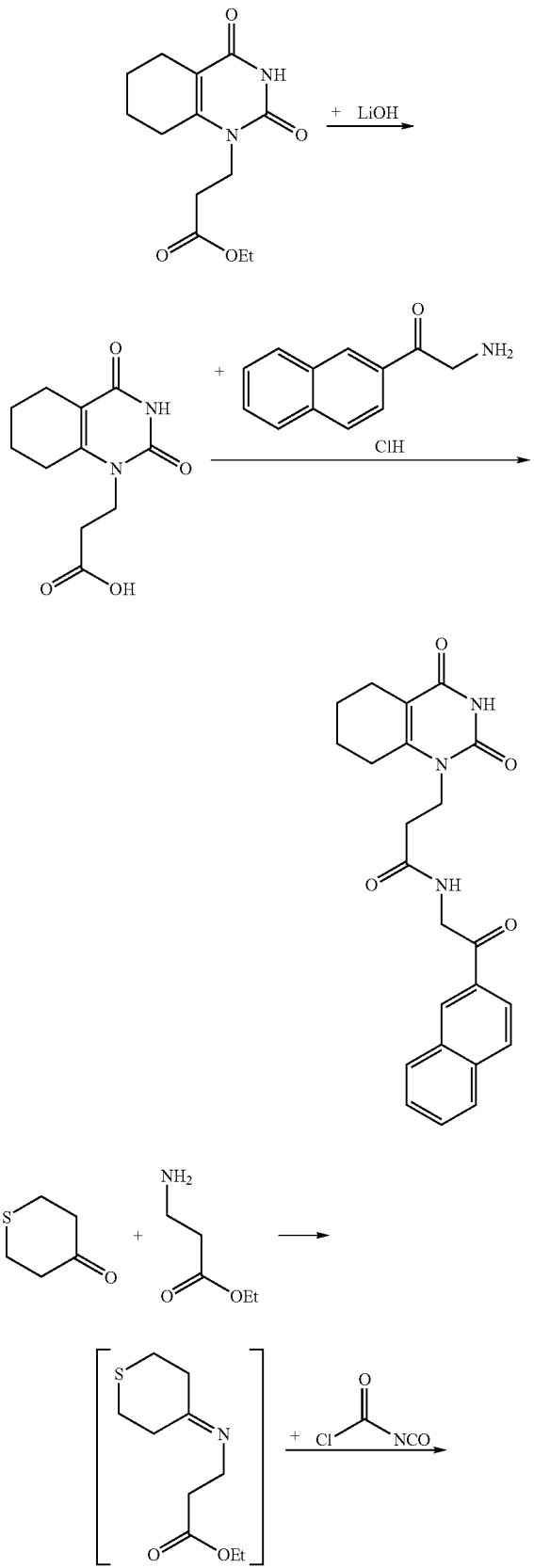
12
-continued
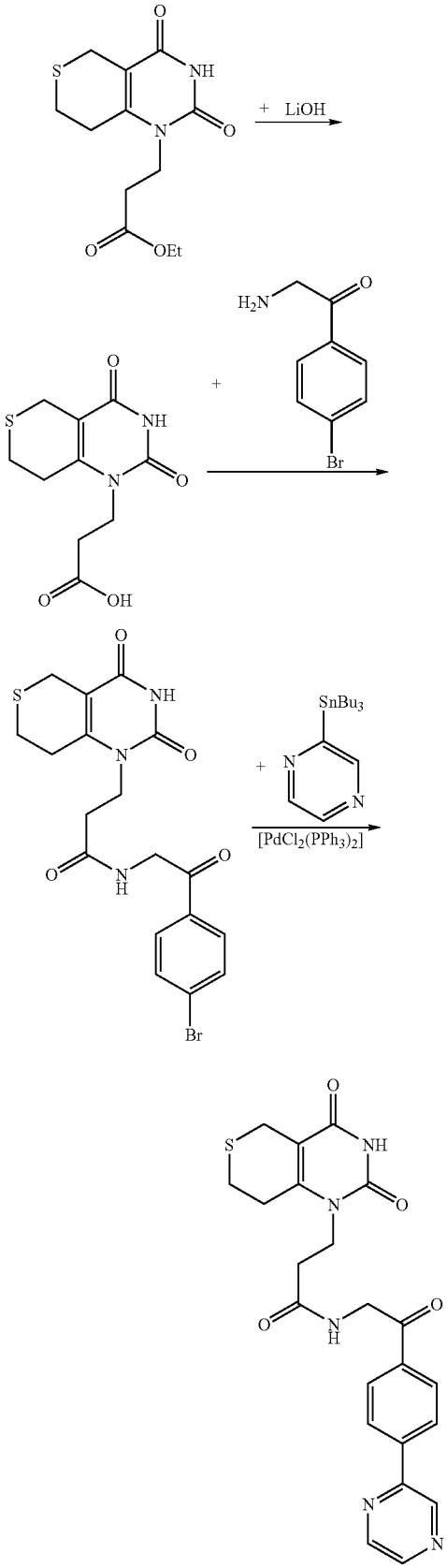

Solvents suitable for the process described above are organic solvents which are inert under the reaction conditions, or water. These include halogenated hydrocarbons, such as dichloromethane, trichloromethane, carbon tetrachloride, 1,2-dichloroethane, trichloroethane, tetrachloroethane, 1,2-dichloroethylene or trichloroethylene, ethers, such as diethyl ether, dioxane, tetrahydrofuran, glycol dimethyl ether or diethylene glycol dimethyl ether, hydrocarbons, such as benzene, xylene, toluene, hexane or cyclohexane, or other solvents, such as dimethylformamide, dimethyl sulphoxide, N-methylpyrrolidone, acetonitrile, pyridine or hexamethylphosphoric triamide, or mixtures thereof.

The reactions are generally carried out in a temperature range of from −78° C. to 150° C., preferably in the range from 0C to 130° C.

The reactions can be carried out at atmospheric, elevated or reduced pressure (for example in the range from 0.5 to 5 bar). In general, they are carried out at atmospheric pressure.

Suitable bases are the customary inorganic or organic bases. These preferably include alkali metal and alkaline earth metal hydroxides, such as, for example, lithium hydroxide, sodium hydroxide or potassium hydroxide, or alkali metal and alkaline earth metal carbonates, such as sodium carbonate or potassium carbonate or sodium methoxide or potassium methoxide or sodium ethoxide or potassium ethoxide or potassium tert-butoxide, or amides, such as sodium amide, lithium-bis-(trimethylsilyl)amide or lithium-diisopropylamide, or amines, such as triethylamine, diisopropylethylamine, diisopropylamine, N-methylmorpholine, 4-dimethylamino-pyridine or pyridine.

Preferred solvent for the reaction of compounds (II) with compounds (III) to give compounds (IV) is toluene. The temperature range for this reaction is in particular between 80° C. and 120° C. Moreover, the reaction can, if appropriate, be promoted by addition of catalytic amounts of acid, preferably organic sulphonic acid, in particular camphorsulphonic acid.

The conversion of compounds (IV) with chlorocarbonyl isocyanate into compounds (V) is preferably carried out in the solvent toluene. Here, the addition of chlorocarbonyl isocyanate is preferably carried out at room temperature and the subsequent reaction in particular in a temperature range between 80° C. and 120° C.

The hydrolysis of compounds (V) to compounds (VI) is carried out by customary methods, for example by treating the esters in inert solvents with acids or with bases, where in the latter case the salts that are initially formed are converted by treatment with acid into the free carboxylic acids. In the case of the t-butyl esters, the hydrolysis is preferably carried out using acids. In the case of the methyl or ethyl esters, the hydrolysis is preferably carried out using bases.

Suitable acids are generally trifluoroacetic acid, sulphuric acid, hydrogen chloride, hydrogen bromide and acetic acid, or their mixture, if appropriate with addition of water. Particular preference is given to using trifluoroacetic acid.

Bases suitable for the hydrolysis are the customary inorganic bases. These preferably include alkali metal hydroxides or alkaline earth metal hydroxides, such as, for example, sodium hydroxide, lithium hydroxide, potassium hydroxide or barium hydroxide, or alkali metal carbonates, such as sodium carbonate or potassium carbonate or sodium bicarbonate. Particular preference is given to using sodium hydroxide or lithium hydroxide.

Solvents suitable for the hydrolysis of water are the customary organic solvents. These preferably include alcohols, such as methanol, ethanol, propanol, isopropanol or butanol, or ethers, such as tetrahydrofuran or dioxane, dimethylformamide, dichloromethane or dimethyl sulphoxide. It is also possible to use mixtures of the solvents mentioned. Preference is given to water/ethanol and, in the case of the reaction with trifluoroacetic acid, to dichloromethane.

When the hydrolyses are carried out, the base or the acid is generally employed in an amount of from 1 to 100 mol, preferably from 1.5 to 40 mol, based on 1 mol of ester.

The hydrolysis is generally carried out in a temperature range of from 0° C. to +100° C.

Preferred solvents for the reaction of compounds (VI) with compounds (VII) or (VIIa) are dichloromethane or dimethylformamide. The reaction is carried out, in particular, at room temperature. Preferred auxiliaries used for this reaction are customary condensing agents, such as carbodiimides, for example N,N'-diethyl-,N,N'-dipropyl-, N,N'-diisopropyl-, N,N'-dicyclohexylcarbodiimide, N-(3-dimethylaminoisopropyl)-N'-ethylcarbodiimide hydrochloride (EDC), or carbonyl compounds, such as carbonyldiimidazole, or 1,2-oxazolium compounds, such as 2-ethyl-5-phenyl-1,2-oxazolium 3-sulphate or 2-tert-butyl-5-methyl-isoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyl-uronium hexafluorophosphate (HATU), or 1-hydroxybenzotriazole. Bases used are alkali metal carbonates, for example sodium carbonate or potassium carbonate, or sodium bicarbonate or potassium bicarbonate, or organic bases, such as trialkylamines, for example triethylamine, N-methylmorpholine, N-methylpiperidine, 4-dimethylaminopyridine or diisopropylethylamine. Particular preference is given to the combination of EDC, N-methylmorpholine, 4-dimethylaminopyridine and 1-hydroxybenzotriazol.

The aryl coupling reaction of compounds (VIIIa) with compounds (IX) is carried out under customary reaction conditions in the presence of a catalyst, preferably in the presence of a transition metal catalyst, in particular in the presence of a palladium catalyst (see, for example, J. Tsuji, Palladium Reagents and Catalysts, J. Wiley & Sons, 1995), preferably in the solvent dimethylformamide. Preferred transition metal catalysts used are palladium(0) or palladium(II) compounds, in particular bis-(triphenylphosphine)-palladium-(II) chloride or tetrakis-(triphenylphosphine)-palladium(0). Preferred metallic or semimetallic groups M in the compounds of the formula (IX) are boron or tin derivatives, for example $B(OH)_2$ or trialkyltin. If organoboron compounds are used (Suzuki coupling, review: N. Miyaura, A. Suzuki, Chem. Rev. 1995, 95, 2457–2483), the reaction is carried out in particular, at a temperature of from 90° C. to 110° C. in the presence of a base, preferably aqueous sodium carbonate solution. If organotin compounds are used (Stille Coupling, review: V. Farina, V. Krishnamurthy, W. J. Scott in: The Stille Reaction, 1998, J. Wiley and Sons, New York), the reaction is carried out, in particular, at a temperature of from 110° C. to 130° C.

Suitable leaving groups Q in compounds of formula (X) are, for example: halogen or 1-imidazolyl. Preference is given to chlorine.

The compounds of the formulae (II), (III), (VII), (VIIa), (IX) and (X) are known to the person skilled in the art or can be prepared by customary methods or similarly to the reaction steps described in the examples.

Surprisingly, the compounds of the formula (I) according to the invention have an unforeseeable useful spectrum of pharmacological activity, and they are therefore particularly suitable for the prophylaxis and/or treatment of disorders.

They can preferably be used in medicaments for the prevention and/or therapy of ischaemic and reperfusion damage in the heart (after an acute infarction), in the brain (after a stroke) or in skeletal muscle, for cardiovascular disorders, such as, for example, unstable angina pectoris and arteriosclerosis, neuronal and neurodegenerative disorders, such as, for example, epilepsy, chronic pain, Alzheimer's disease and Parkinson's disease, traumatic brain injuries, septic shock, and also arthritis, diabetes, chronic colitis, sudden deafness, inflammable pulmonary disorders, such as, for example, asthma and chronic bronchitis, and cancer.

The present invention also relates to the use of the substances of the formula (I) for preparing medicaments and to pharmaceutical compositions for the prophylaxis and/or treatment of the clinical pictures mentioned above.

The present invention furthermore relates to a method for the prophylaxis and/or treatment of the clinical pictures mentioned above using the substances of the formula (I).

In addition, the compounds according to the invention can also be used for the treatment of acute myocardial infarction, including in combination with one or more of the following medicaments which are used for the standard therapy of acute myocardial infarction: calcium channel blockers (such as, for example, nifedipine, diltiazem, verapamil), nitrovasodilators (such as, for example, isosorbide dinitrate, glycerol trinitrate, isosorbide 5-mono-nitrate, molsidomine), beta blockers, (such as, for example, metoprolol, atenolol, propranolol, solatol), platelet aggregation inhibitors (such as, for example, acetylsalicylic acid, triclopidine, clopidogrel), thrombolytics (fibrinolytics) (such as, for example, streptokinase, alteplase, reteplase, urokinase, anistreplase), anticoagulants (such as, for example, heparin, warfarin, phenprocoumarin, low-molecular-weight heparins), ACE inhibitors (such as, for example, enalapril), glycoprotein IIb/IIIa receptor antagonists (such as, for example, tirofiban, eptifibatide), antiarrhythmics (such as, for example, lidocaine, amiodarone) and beta-adrenergic agonists (such as, for example, dopamine, dobutamine).

A Evaluation of the Physiological Activity

1) Test Description PARS Inhibition Test (in Vitro)

The activity of substances as PARS inhibitors is tested in accordance with the method of Ushiro [Ushiro et al., J. Biol. Chem., 262, 2352–2357 (1987)]. To this end, recombinantly expressed (Bac-To-Bac, Baculo virus expression system; Instruction Manual; Life Technologies) human PARS enzyme is activated in a buffer which contains radioactively labelled [$^{14}$C]—NAD$^+$. The poly(ADP-ribose) units that are synthesized are precipitated using trichloroacetic acid, and the proportion of labelled protein is determined by scintillation measurements. Incubation of PARS with inhibitors leads to a decrease in the proportion of labelled protein and thus to a reduced radioactivity.

Inhibition of the PARS activity can be represented as a percentage of PARS inhibition in incubation with different substances or as the concentration at which 50% of the enzyme is inhibited, i.e. as IC$_{50}$ value.

Material
Buffer: 100 mM 2-amino-2-hydroxymethyl-1,3-propanediol (tris)-HCl, pH 7.4
  10 mM MgCl$_2$
  1 mM dithiothreitol (DTT)
  Tris-HCl and MgCl$_2$ are dissolved in water, DTT is added from an aqueous 100 mM stock solution (stored at −20° C.) and the pH is adjusted with concentrated HCl to 7.4.
DNA: 1 mg/ml of calf thymus DNA
  1 mg/ml of calf thymus DNA (from Sigma) is dissolved in water and sonicated to induce strand breaks. 500 µl aliquots were stored at −20° C.
Histones: 10 mg/ml of type IIA histones, calf thymus
  10 mg/ml of lyophilized histones (from Sigma) are dissolved in water.
  500 µl aliquots are stored at −20° C.
NAD$^+$ Mix: 2 mM NAD$^+$ in buffer,
  NAD$^+$ (from Sigma) solutions are prepared freshly before each test.
  In each case 3 µl of labelled [$^{14}$C]—NAD$^+$ (2.8 kBq, from Amersham) are added to 7 µl of cold NAD$^+$ solution.
Trichloroacetic acid (TCA): TCA is stored at 4° C. as a 10% strength by weight solution.
PARS: Human PARS protein is expressed recombinantly in the baculovirus system (Bac-To-Bac, Baculo virus expression system; Instruction Manual; Life Technologies) and purified. 500 µl aliquots are stored at −80° C.

Methods

The compounds to be tested are dissolved in DMSO (dimethyl sulphoxide) at a concentration of 10 mM. The assay is carried out in deep 96-well plates. Per well, 70 µl of buffer, 10 µl of DNA, 10 µl of histones, 10 µl of NAD$^+$/[$^{14}$C]—NAD$^+$ mix and 0.5–5 µl of PARS (about 10,000 cpm/test) are combined with 1 µl of the compounds (final concentration 0.001–10 µM), to give a total volume of about 110 µl. The mixture is incubated at room temperature for 10 min, and 1 ml of ice-cold TCA solution is then added, and the precipitated labelled proteins are sucked onto a filter paper (printed filter mat A; from Wallac) using a harvester (from Scatron). The filter is dried, sealed together with a scintillation sheet (Multilex A; from Wallac) and measured in a β counter for 1 min per well.

Results of the PARS Inhibition Test

In addition to the substances described in this application, the known PARS inhibitor 1,5-dihydroxyisoquinoline (DHCH) is tested as reference substance. The results of the test are stated as IC$_{50}$ values for the inhibition of PARS.

The results are shown in Table 1:

TABLE 1

| PARS inhibition (in vitro) | |
|---|---|
| Example | IC$_{50}$ [nM] |
| DHCH | 300 |
| 4 | 20 |
| 6 | 8.5 |
| 7 | 12 |
| 15 | 15 |
| 20 | 20 |
| 54 | 80 |

2) Test Description Cell Protection Assay (in Vitro)

In accordance with a method described by Bowes [Bowes et al., Br. J. Pharmacol., 124, 1760–1766 (1998)], the ability of PARS inhibitors to protect cells against cell death induced by incubation with H$_2$O$_2$ is examined in a cell protection assay. Incubation of endothelial cells with H$_2$O$_2$ results in the generation of DNA strand breaks which in turn activate PARS, resulting in a drastic energy decrease in the cells and in cell death. Living cells are quantified by a fluorimetric redox indicator (Alamar blue), which is converted in the electron transport system of the mitochondria.

Specifically, 7500 MHEC5-T cells/well (DSM ACC 336; German collection of microorganisms and cell cultures) are sown in 4 replications on a 96-well plate. After 24 hours, the cells are incubated with 3 mM aqueous $H_2O_2$ solution and differing concentrations of the substances in the presence of 6% by volume of Alamar blue solution in the medium at 37° C. for 5 hours. The reference substance used is 10 µM 1,5-dihydroxyisoquinoline (DHCH) solution. After the incubation, the fluorescence is measured at an excitation wavelength of 530–560 nm and an emission wavelength of 590 nm. The percentage for the cell protection is calculated as the difference between the living cells treated only with $H_2O_2$ and the cells treated with $H_2O_2$ and PARS inhibitors. The internal standard used is 10 µM DHCH, which is defined as 100% protection. The results obtained for the other substances are compared to this value.

Results of the Cell Protection Assays:

Examples of the protection of endothelial cells by PARS inhibitors are listed in Table 2 below. The $EC_{50}$ values indicate the concentration at which 50% of maximum cell protection is reached, maximum protection by 10 µM DHCH being defined as 100%. DHCH has an $EC_{50}$ value of 2 µM.

TABLE 2

Cell protection (in vitro)

| Example | $EC_{50}$ [nM] |
|---|---|
| 5 | 0.07 |
| 7 | 0.09 |
| 12 | 0.095 |
| 15 | 0.05 |
| 20 | 0.1 |
| 24 | 0.02 |
| 30 | 0.1 |
| 32 | 0.2 |
| 40 | 0.09 |

2) Test Description "Working Heart" Model (in Vivo)

For tests on isolated hearts in the "working heart" mode [Bardenheuer and Schrader, Circulation Res., 51, 263 (1983)], isolated hearts of rats are subjected to a 60-minute "low-flow" phase to generate global ischaemia, and the action of the substances with respect to the reestablishment of the pressure in the left ventricle (LVPmax) and the contractile force (dP/dt) during the reperfusion phase is examined. The control substance used is 1,5-dihydroxyisoquinoline.

The present invention also relates to medicaments and pharmaceutical compositions comprising at least one compound of the formula (I), preferably together with one or more pharmacologically acceptable auxiliaries or excipients, and to their use for the abovementioned purposes.

The active compound can act systemically and/or locally. To this end, it can be administered in a suitable manner, such as, for example, orally, parenterally, pulmonarily, nasally, sublingually, lingually, buccally, rectally, transdermally, conjunctivally, otically or as an implant.

For these administration routes, the active compound can be administered in suitable administration forms.

Administration forms suitable for oral administration are known administration forms which release the active compound rapidly and/or in modified form, such as, for example, tablets (uncoated and also coated tablets, for example enterically coated tablets), capsules, sugar-coated tablets, granules, pellets, powders, emulsions, suspensions and solutions.

Parenteral administration can be effected by circumventing a bioabsorption step (in an intravenous, intraarterial, intracardial, intraspinal or intralumbal manner), or via bioabsorption (intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates and sterile powders.

Medicinal forms suitable for the other administration routes are, for example, medicinal forms for inhalation (inter alia powder inhalators, nebulizers), nasal drops/solutions, sprays; tablets to be administered lingually, sublingually, or capsules to be administered buccally, suppositories, preparations for ears or eyes, vaginal capsules, aqueous suspensions (lotions, agitated mixtures), lipophilic suspensions, ointments, creams, milk, pastes, powder for spreading or implants.

The active compounds can be converted in a manner known per se into the administration forms listed. This is effected using inert non-toxic, pharmaceutically suitable auxiliaries. These include, inter alia, excipients (for example microcrystalline cellulose), solvents (for example liquid polyethylene glycols), emulsifiers (for example sodium dodecyl sulphate), dispersants (for example polyvinylpyrrolidone), synthetic and natural biopolymers (for example albumin or cyclodextrins), stabilizers (for example antioxidants such as ascorbic acid), colorants (for example inorganic pigments, such as iron oxides), or flavour- and/or odour-masking substances.

In the pharmaceutical preparations listed above, the therapeutically active compounds should be present in a concentration of from about 0.1 to 99.5, preferably from about 0.5 to 95, % by weight of the total mixture, i.e. the active compound should be present in amounts sufficient to achieve the dosage range indicated.

In addition to the compounds of the formula (I) according to the invention, the pharmaceutical preparations listed above may also comprise other pharmaceutically active compounds.

In general, it has been found to be advantageous both in human and veterinary medicine to administer the active compound(s) according to the invention in total amounts of from about 0.01 to about 100, preferably from 0.05 to 50, mg/kg of body weight per 24 hours, if appropriate in the form of a plurality of individual doses, to obtain the desired results. An individual dose preferably comprises the active compound(s) according to the invention in amounts of from about 0.01 to 50, in particular from 0.1 to 10, mg/kg of body weight.

In spite of this, it may be necessary, if appropriate, to depart from the amounts mentioned, namely depending on the body weight or on the type of administration route, on the individual response to the medicament, the manner of its formulation and the time or interval at which administration takes place. Thus, in some cases it may be adequate to manage with less than the abovementioned minimum amount, while in other cases the upper limit mentioned has to be exceeded.

Unless indicated otherwise, all percentages in the examples below are based on weight; in the case of solvent mixtures, the ratios given are by volume.

B Preperation Examples

In the description of the examples, the following abbreviations are used:
DMF=N,N-dimethylformamide,
DMAP=4-dimethylaminopyridine
EDC=N-(3-dimethylaminopropyl)-N'-ethylcarbodiimide hydrochloride
Z=benzyloxycarbonyl Starting Materials The heteroarylpiperazines required as starting materials for some synthesis examples can be prepared by reacting the corresponding chloroheteroaromatic compounds with piperazine.

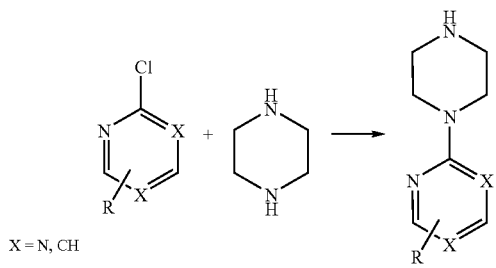

X = N, CH

N,N-Diethyl-2-(1-piperazinyl)-4-pyrimidinamine

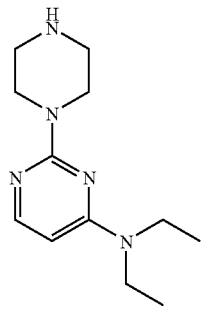

A solution of piperazine (5.8 g, 67.33 mmol) and N-(2-chloro-4-pyrimidinyl)-N,N-diethylamine (5.0 g, 26.93 mmol; preparation see: L. Strekowski, Pol. J. Chem. 1980, 54, 1557–62) in ethanol (200 ml) is heated at 100° C. for 16 hours. The mixture is then concentrated under reduced pressure and extracted with water/ethyl acetate. The organic phase is washed with saturated sodium chloride solution, dried over sodium sulphate, filtered and concentrated under reduced pressure. Silica gel chromatography (mobile phase: dichloromethane/methanol) gives 4.01 g of the product (63%) as a yellow oil.

$^1$H-NMR (200 MHz, DMSO-$d_6$, δ/ppm): 7.79 (1H, d); 5.87 (1H, d); 3.50–3.63 (4H, m); 3.31–3.50 (4H, m); 2.63–2.77 (4H, m); 1.08 (6H, t).

MS (ESI+): 236 (M+H$^+$).

The chloroheteroatomic compounds required for the preparation of various heteroaryl piperazines can be prepared, for example, analogously to the following literature references:
2-chloro-5-(4-chlorophenyl)pyrimidine (D. J. Brown, T.-C. Lee, J. Chem. Soc. C 1970, 214–19)
2-chloro-1,3,5-triazine (from 2-(phenylsulphanyl)-1,3,5-triazine, G. Porrozzi et al., Gazz. Chim. Ital. 1980, 110, 609–12)
6-chloro-2-pyridinamine (J. J. Kaminski et al., J. Med. Chem. 1987, 30, 2047–51)
2-chloro-4-methoxyquinazoline (N. A. Lange, F. E. Sheibley J. Am. Chem. Soc. 1931, 53, 3867–75)

2-chloroethyl glycinate can be prepared according to H. Kunz, M. Buchholz, Chem. Ber. 1979, 112,2145–2157.

The 3-[4-(5-fluoro-2-pyrimidinyl)-1-piperazinyl]-3-oxo-1-propaneamine required for preparing Synthesis Examples 138 and 166 is synthesized analogously to Example 4b*) from 5-fluoro-2-(1-piperazinyl)pyrimidine by reaction with N-[(benzyloxy)carbonyl]-β-alanine and subsequent removal of the protective group by catalytic hydrogenation.

SYNTHESIS EXAMPLES

Example 1

3-(2,4-dioxo-3,4,5,6,7,8-hexahydro-1(2H)-quinazolinyl)-N-(2-[2-npahthyl]-2-oxo-1-ethyl)propanecarboxamide

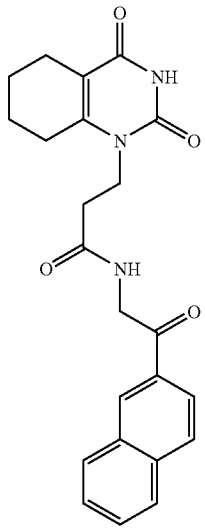

a) Ethyl 3-(2,4-dioxo-3,4,5,6,7,8-hexahydro-1(2H)-quinazolinyl)propane carboxylate The free amine of 15.36 g (100.0 mmol) of ethyl 3-alanine hydrochloride and 10.36 ml (100.0 mmol) of cyclohexanone are initially charged in 200 ml of toluene and admixed with a spatula-tip of camphorsulphonic acid, and the mixture is heated under reflux for 1.5 hours using a water separator. The reaction solution is then allowed to cool under argon, and 8.05 ml (100.0 mmol) of chlorocarbonyl isocyanate are then added at room temperature. The mixture is heated under reflux for one hour and then, after cooling off the reaction mixture, treated with saturated aqueous sodium dihydrogenphosphate solution and extracted repeatedly with ethyl acetate. The organic phase is washed with saturated aqueous sodium chloride solution and dried over sodium sulphate. The solvent is removed and the crude product is then purified by column chromatography (silica gel, methylene chloride/methanol 500:1–20:1). The product fraction is concentrated and dried under reduced pressure. This gives 14.44 g (54.2 mmol; 54% yield) of a pale yellow solid.

$R_f$ value: 0.31 (ethyl acetate).

$^1$H-NMR (200 MHz, DMSO-$d_6$, δ/ppm): 11.20 (s, 1H), 4.07 (q, 2H), 3.95 (t, 2H), 2.65–2.53 (m, 4H), 2.19 (t, 2H), 1.68 (m, 2H), 1.55 (m, 2H), 1.18 (t, 3H).

MS (ESI): 284.2 (M+NH$_4^+$), 267.2 (M+H$^+$).

b) 3-(2,4-dioxo-3,4,5,6,7,8-hexahydro-1(2H)-quinazolinyl)-propanecarboxylic acid A solution of 14.4 g (54.1 mmol) of ethyl 3-(2,4-dioxo-3,4,5,6,7,8-hexahydro-1(2H)-quinazolinyl)-propanecarboxylate and 6.47 g (270.4 mmol) of lithium hydroxide in 200 ml of a mixture of ethanol and water (4:1) are heated under reflux for one hour. The cooled solution is then mixed with 1 M hydrochloric acid until a pH of 1 is reached, and then concentrated to dryness. The resulting residue is dissolved in about 20 ml of water. On addition of ether, the product is obtained as a precipitate which is filtered off with suction and dried under reduced pressure. This gives 10.2 g (42.8 mmol, 79% yield) of a pale yellow solid.

$^1$H-NMR (200 MHz, DMSO-d$_6$, δ/ppm): 12.38 (s, 1H), 11.19 (s, 1H), 3.92 (t, 2H), 2.60–2.53 (m, 4H), 2.19 (t, 2H), 1.69 (m, 2H), 1.55 (m, 2H).

MS (ESI): 256 (M+NH$_4^+$), 239 (M+H$^+$).

c) 3-(2,4-dioxo-3,4,5,6,7,8-hexahydro-1(2H)-quinazolinyl)-N-(2-[2-naphthyl]-2-oxo-1-ethyl)propanecarboxamide 70 μl (0.42 mmol) of N,N-diisopropylamine and a spatula-tip of 4-dimethylaminopyridine are added to a solution of 40 mg (0.17 mmol) of 3-(2,4-dioxo-3,4,5,6,7,8-hexahydro-1(2H)-quinazolinyl)propanecarboxylic acid and 38 mg (0.17 mmol) of 2-(2-naphthyl)-2-oxo-1-ethaneaminium chloride (from Bionet) in 5 ml of methylene chloride. At 0° C., this reaction solution is admixed with 47 mg (0.18 mmol) of 1,3-dicyclohexylcarbodiimide and stirred at room temperature for 18 hours. The reaction mixture is then partitioned between methylene chloride and an aqueous buffer solution with pH=2. The organic phase is dried over sodium sulphate and concentrated. The resulting residue is separated by preparative HPLC (column: Kromasil 100 C 18, 5 mm, 250×40 mm; mobile phase: acetonitrile/water; flow rate: 25 ml/min; UV detection at 210 nm). This gives 33 mg (0.08 mmol, 48% yield) of the product as an amorphous solid.

R$_f$ value: 0.24 (methylene chloride/methanol 20:1).

$^1$H-NMR (200 MHz, DMSO-d$_6$, δ/ppm): 11.21 (s, 1H), 8.72 (s, 1H), 8.46 (t, 1H), 8.11–7.95 (m, 3H), 7.72–7.60 (m, 3H), 4.76 (d, 2H), 3.95 (t, 2H), 2.64–2.5 (m, 4H), 2.21 (t, 2H), 1.70 (m, 2H), 1.57 (m, 2H).

MS (ESI): 406.8 (M+H$^+$).

Example 2

3-(2,4-dioxo-3,4,7,8-tetrahydro-2H-thiopyranol[4,3-d]pyrimidin-1(5H)-yl)-N-(2-oxo-{2-methylimidazo[1,2-a]pyridin-3-yl}ethyl)propanecarboxamide

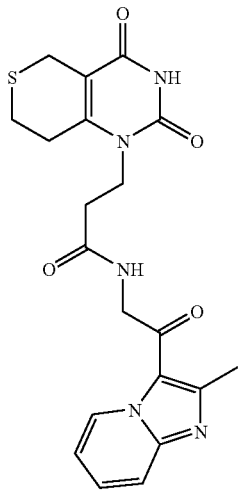

a) tert-Butyl 3-(2,4-dioxo-3,4,7,8-tetrahydro-2H-thiopyrano[4,3-d]pyrimidin-1(5H)-yl)propanecarboxylate The free amine of 3.09 g (17.0 mmol) of t-butyl 3-alanine hydrochloride and 1.98 g (17.0 mmol) of tetrahydro-4-thiopyranone are initially charged in 60 ml of toluene and admixed with a spatula-tip of camphorsulphonic acid, and the mixture is heated under reflux for one hour, using a water separator. The reaction solution is then allowed to cool under argon, and, at room temperature, 1.37 ml (17.0 mmol) of chlorocarbonyl isocyanate are added. The mixture is heated under reflux for one hour and then, after cooling off the reaction mixture, admixed with saturated aqueous sodium dihydrogenphosphate solution and extracted repeatedly with ethyl acetate. The organic phase is washed with saturated aqueous sodium chloride solution and dried over sodium sulphate. The solvent is removed, and the product is dried under reduced pressure. This gives 5.20 g (16.6 mmol; 98% yield) of a yellow solid.

R$_f$ value: 0.51 (ethyl acetate).

$^1$H-NMR (200 MHz, DMSO-d$_6$, δ/ppm): 11.46 (s, 1H), 3.93 (t, 2H), 3.34 (s, 2H), 2.86 (s, 4H), 2.55 (t, 2H), 1.40 (s, 9H).

MS (ESI): 330.4 (M+NH$_4^+$), 313.3 (M+H$^+$).

b) 3-(2,4-dioxo-3,4,7,8-tetrahydro-2H-thiopryano[4,3-d]pyrimidin-1(5H)-yl)-propanecarboxylic acid A solution of 5.2 g (16.6 mmol) of tert-butyl 3-(2,4-dioxo-3,4,7,8-tetrahydro-2H-thiopyrano[4,3-d]pyrimidin-1(5H)-yl)propanecarboxylate and 77 ml (998.7 mmol) of trifluoroacetic acid in 200 ml of methylene chloride is stirred at room temperature for 2 hours. The solution is then concentrated to dryness, and the resulting residue is dried under reduced pressure. This gives 4.2 g (16.64 mmol, 99% yield) of a brown resin which crystallizes slowly.

$^1$H-NMR (200 MHz, DMSO-d6, δ/ppm): 11.39 (s, 1H), 3.95 (t, 2H), 3.34 (s, 2H), 2.87 (s, 4H), 2.57 (t, 2H) COOH was not observed.

MS (ESI): 274 (M+NH$_4^+$), 257 (M+H$^+$).

c) 2-Bromo-1-(2-methylimidazo[1,2-a]pyridin-3-yl)ethanone 1.75 g (10.1 mmol) of 1-(2-methylimidazo[1,2-a]pyridin-3-yl)ethanone (from Maybridge) are initially charged in 20 ml of concentrated hydrobromic acid. At 60° C., a solution of 0.56 ml (11.0 mmol) of bromine and 10 ml of concentrated hydrobromic acid is added dropwise over a period of one hour to this solution. The mixture is allowed to stand at 5° C. over night and the product is filtered off and washed with aqueous sodium bicarbonate solution and water. This gives 1.1 g (4.3 mmol, 43% yield) of product.

R$_f$ value: 0.34 (methylene chloride/methanol 20:1).

$^1$H-NMR (200 MHz, DMSO-d$_6$, δ/ppm): 9.76 (d, 1H), 7.98 (m, 2H), 7.58 (m, 1H), 4.79 (m, 2H), 2.80 (s, 3H).

MS (ESI): 252.9 (M+H$^+$).

d) 2-Amino-1-(2-methylimidazo[1,2-a]pyridin-3-yl)ethanone hydrochloride

A filtered solution of 1.00 g (3.95 mmol) of 2-bromo-1-(2-methylimidazo[1,2-a]pyridin-3-yl)-ethanone in chloroform is added to a solution of 3.00 g (21.4 mmol) of hexamethylenetetramine. The solution is stirred for one hour and then cooled to 0° C., and the resulting precipitate is filtered off. The precipitate is dissolved in 10 ml of concentrated hydrochloric acid and stirred at room temperature for one hour. The mixture is then diluted with 20 ml of ethanol and concentrated to dryness, and the residue is recrystallized from isopropanol/conc. hydrochloric acid 100:1. The product is filtered off and washed with a little isopropanol. This gives 279 mg (1.23 mmol, 31.3% yield) of a white microcrystalline solid.

$^1$H-NMR (200 MHz, DMSO-d$_6$, δ/ppm): 9.70 (d, 1H), 8.7 (br.s., amine protons), 7.94 (m, 2H), 7.53 (m, 1H), 4.51 (m, 2H), 2.85 (s, 3H); additionally signals for ammonium chloride

MS (ESI): 190.3 (M+H$^+$).

e) 3-(2,4-dioxo-3,4,7,8-tetrahydro-2H-thiopyrano[4,3-d]pyrimidin-1(5H)-yl)-N-(2-oxo-{2-methylimidazo[1,2-a]pyridin-3-yl}ethyl)propanecarboxamide 58 mg (0.43 mmol) of 1-hydroxy-1H-benzotriazole, 86 mg (0.45 mmol) of EDC, 9 mg (0.08 mmol) of 4-dimethylaminopyridine and 150 μl (1.37 mmol) of 4-methylmorpholine are added successively to a solution of 100 mg (0.39 mmol) of 3-(2,4-dioxo-3,4,7,8-tetrahydro-2H-thiopyrano[4,3-d]pyrimidin-1(5H)-yl)propanecarboxylic acid and 88 mg (0.39 mmol) of 2-amino-1-(2-methylimidazo[1,2-a]pyridin-3-yl)ethanone hydrochloride in 5 ml of dimethylformamide. The reaction mixture is stirred at room temperature for 18 hours and then poured onto ice. The aqueous phase is extracted with diethyl ether and methylene chloride and the combined organic phases are dried over sodium sulphate. The residue obtained after concentration is separated by preparative HPLC (column: Kromasil 100 C 18, 5 mm, 250×40 mm; mobile phase: acetonitrile/water; flow rate: 25 ml/min; UV detection at 210 nm). This gives 16 mg (0.04 mmol, 9% yield) of the product as an amorphous solid.

$R_f$ value: 0.12 (methylene chloride/methanol 20:1).

$^1$H-NMR (200 MHz, DMSO-$d_6$, δ/ppm): 11.43 (s, 1H), 9.62 (d, 1H), 8.44 (t, 1H), 7.74 (d, 1H), 7.62 (t, 1H), 7.24 (dt, 1H), 4.49 (d, 2H), 3.98 (t, 2H), 3.37 (s, 2H), 2.86 (m, 4H), 2.74 (s, 3H), 2.61 (t, 2H).

MS (ESI): 428.2 (M+H$^+$).

Example 3

3-(2,4-Dioxo-3,4,7,8-tetrahydro-2H-thiopyrano[4,3-d]pyrimidin-1(5H)-yl)-N-(2-(3,4-dichlorophenyl)-2-hydroxy-1-ethyl)propanecarboxamide

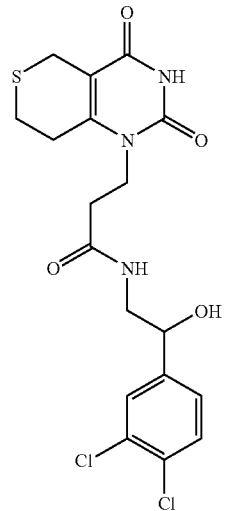

116 mg (0.86 mmol) of 1-hydroxy-1H-benzotriazole, 172 mg (0.90 mmol) of EDC, 18 mg (0.16 mmol) of 4-dimethylaminopyridine and 260 μl (2.34 mmol) of 4-methylmorpholine are added successively to a solution of 200 mg (0.78 mmol) of 3-(2,4-dioxo-3,4,7,8-tetrahydro-2H-thiopyrano[4,3-d]pyrimidin-1(5H)-yl)propanecarboxylic acid and 189 mg (0.78 mmol) of 2-amino-1-(3,4-dichlorophenyl)ethanol hydrochloride (H. Bercher et al., Pharmazie 1976, 31, 351–354) in 10 ml of dimethylformamide. The reaction mixture is stirred at room temperature for 18 hours and then poured onto ice. The aqueous phase is then extracted with diethyl ether and methylene chloride and the combined organic phases are dried over sodium sulphate. The residue obtained after concentration is purified by column chromatography (silica gel, methylene chloride/methanol 50:1–20:1). The product fraction is concentrated and dried under reduced pressure. This gives 68 mg (0.15 mmol, 20% yield) of the product as an amorphous white solid.

$R_f$ value: 0.02 (methylene chloride/methanol 20:1).

$^1$H-NMR (200 MHz, DMSO-$d_6$, δ/ppm): 11.43 (s, 1H), 8.09 (t, 1H), 7.57 (m, 2H), 7.27 (d, 1H), 5.52 (m, 2H), 4.61 (q, 1H), 3.89 (t, 2H), 3.22 (t, 2H), 2.86 (s, 4H) 2.41 (t, 2H) OH was not observed.

MS (ESI): 461.2 (M+NH$_4^+$), 444.1 (M+H$^+$).

Example 4

3-(2,4-Dioxo-3,4,7,8-tetrahydro-2H-thiopyrano[4,3-d]pyrimidin-1(5H)-yl)-N-(2-oxo-2-[4-(2-pyrimidinyl)-1-piperazinyl]ethyl)propanecarboxamide

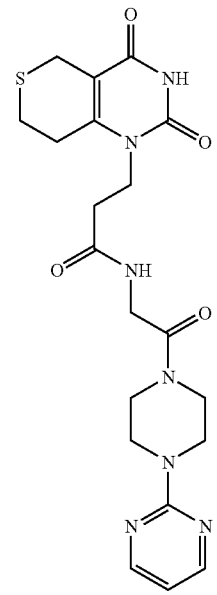

a) 2-[4-(chloroacetyl)-1-piperazinyl]pyrimidine

Chloroacetyl chloride (1.16 ml, 14.62 mmol) is added to an ice-cooled solution of 2-(1-piperazinyl)pyrimidine (2.0 g, 12.18 mmol) in dichloromethane (20 ml) and triethylamine (5.09 ml, 36.54 mmol), and the mixture is stirred for 5 minutes and then warmed to room temperature. After 30 min at RT, water (50 ml) is then added to the mixture, which is extracted twice with methylene chloride (50 ml). The organic phase is washed with saturated sodium chloride solution. Drying of the organic phase over sodium sulphate, filtration, concentration under reduced pressure and silica gel chromatography (mobile phase: cyclohexane/ethyl acetate=10:1 to 1:1) gives 2.05 g (70%) of product as a colourless solid.

MS (EI): 242 (M+H)$^+$ $^1$H-NMR (d$^6$-DMSO): 3.45–3.65 (4H, m); 3.65–3.85 (4H, m); 4.43 (2H, s); 6.79 (1H, t); 8.39(2H, d)

b) 2-Oxo-2-[4-(2-pyrimidinyl)-1-piperazinyl]ethylamine hydrochloride

A solution of the compound from Example 4a) (0.9 g, 3.74 mmol) in chloroform (4 ml) is added to a solution of hexamethylenetetramine (0.58 g, 4.11 mol) in ethanol (25 ml) and the mixture is then stirred at RT for 10 min. Sodium iodide (0.56, 3.74 mmol) is then added, and the mixture is stirred at RT overnight. Sodium iodide (0.62 g, 4.15 mmol) is then added, and the mixture is stirred at RT overnight. The resulting suspension is cooled (with ice) and filtered. The residue is washed with ice-cold ethanol (10 ml), dried, dissolved in a mixture of ethanol (10 ml) and concentrated hydrochloric acid (2 ml) and stirred at 50° C. for 3 hours.

The resulting suspension is also cooled (with ice) and filtered. The filtrate is then concentrated under reduced pressure and recrystallized from a mixture of isopropanol/concentrated hydrochloric acid (ratio 100:1). The product is obtained as a colourless solid (1.03 g, 79%). The resulting product contains as an impurity traces of ammonium chloride; however, these do not have to be removed for the next reaction step.

MS (ESI): 222.1 (M—Cl)$^+$ $^1$H-NMR (d$^6$-DMSO): 3.45–3.55(2H, m); 3.56–3.62 (2H, m); 3.70–4.0 (6H, m); 6.69 (1H, t); 8.18 (br.s, amine protons); 8.42 (2H, d); additionally signals for ammonium chloride c) 3-(2,4-Dioxo-3,4,7,8-tetrahydro-2H-thiopyrano[4,3-d]pyrimidin-1(5H)-yl)-N-(2-oxo-2-[4-(2-pyrimidinyl)-1-piperazinyl]ethyl]propanecarboxamide 1-Hydroxybenzotriazole (293 mg, 2.17 mmol) and EDC (434 mg, 2.27 mmol) are added to a solution of the compound from Example 2b) (505 mg, 1.97 mmol) in dimethylformamide (20 ml) and the mixture is stirred at RT for 10 min. N-methylmorpholine (0.87 ml, 7.89 mmol), the compound from Example 4b) (1.03 g, 2.96 mmol) and a spatula-tip of DMAP are then added and the mixture is stirred at room temperature overnight. Following filtration, the solution is directly separated by preparative HPLC (column: Kromasil 100 C 18, 5 µm, 250×40 mm; mobile phase: acetonitrile/water; flow rate: 25 ml/min; UV detection at 210 nm). Following concentration under reduced pressure, 369 mg (40.7%) of product are obtained as an amorphous solid.

MS (ESI+): 460.3 (M+H$^+$)

$^1$H-NMR (d$^6$-DMSO): 2.45–2.60 (2H, m); 2.80–2.95 (4H, m); 3.30–3.40 (2H, m); 3.45–3.60 (4H, m); 3.65–3.83 (4H, m); 3.86–4.05 (4H, m); 6.68 (1H, t), 8.20 (1H, t); 8.39(2H, d); 11.41 (1H, s)

The free amine 2-oxo-2-[4-(2-pyrimidinyl)-1-piperazinyl]ethylamine [4b*] which corresponds to the compound from Example 4b can also be prepared by an alternative route via the corresponding Z-protected compound [4a*].

4a*) N-Z-2-Oxo-2-[4-(2-pyrimidinyl)-1-piperazinyl]ethylanine

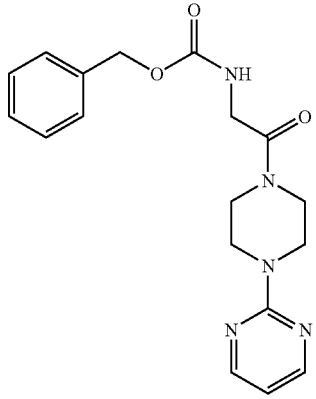

1-Hydroxy-1H-benzotriazole (0.42 g, 3.09 mmol) and EDC (0.62 g, 3.23 mmol) are added to a solution of 1-(2-pyrimidinyl)-piperazine dihydrochloride (1.0 g, 4.22 mmol) in DMF (10 ml). N-Z-Glycine (0.59 g, 2.81 mmol), N-methylmorpholine (1.85 ml, 16.87 mmol) and a catalytic amount of DMAP are then added, and the mixture is stirred at room temperature overnight. The reaction mixture is poured into 50 ml of water and stirred at room temperature for 1 hour. The precipitate is filtered off with suction, washed with 5 ml of water and 5 ml of diethyl ether and dried under reduced pressure. This gives 852 mg (85%) of the product as a colourless solid.

$^1$H-NMR (200 MHz, DMSO-d$_6$, δ/ppm): 8.39 (2H, d); 7.22–7.44 (5H, m); 6.67 (1H, t); 5.03 (2H, s); 3.92 (2H, d); 3.40–3.61 (4H, m), 3.62–3.84 (4H, m).

MS (ESI+): 356 (M+H$^+$).

4b*) 2-Oxo-2-[4-(2-pyrimidinyl)-1-piperazinyl]ethylamine

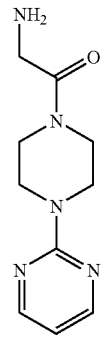

Palladium on carbon (85 mg, 10% by weight of Pd) is added to a solution of the compound from Example 4a*) (850 mg, 2.39 mmol) in methanol (20 ml) and the mixture is hydrogenated under a hydrogen atmosphere of 3 bar for 3 hours. The mixture is then filtered off through Celite and concentrated under reduced pressure. Silica gel chromatography (mobile phase: dichloromethane/methanol/triethylamine) gives 517 mg of the product as a colourless solid.

$^1$H-NMR (200 MHz, DMSO-d$_6$, δ/ppm): 8.39 (2H, d); 6.67 (1H, t); 2.80–3.85 (12H, m, strongly overlapping signals).

MS (ESI+): 222.1 (M+H$^+$).

Example 5

3-(2,4-Dioxo-3,4,7,8-tetrahydro-2H-thiopyrano [4,3-d]pyrimidin-1(5H)-yl)-N-(2-oxo-2-[4-(2-pyrazinyl)phenyl]ethyl)propanecarboxamide

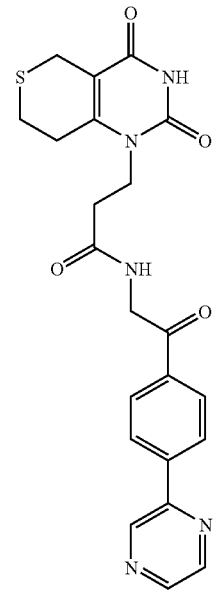

a) 3-(2,4-Dioxo-3,4,7,8-tetrahydro-2H-thiopyrano [4,3-d]pyrimidin-1(5H)-yl)-N-(2-oxo-2-[4-bromophenyl]ethyl)propanecarboxamide is prepared analogously to the procedure for the compound from Example 4c) from 2-amino-1-(4-bromophenyl)ethanone and the compound from Example 2b).

MS (DCI): 469.1 (M+NH$_4^+$)

¹H-NMR (d₆-DMSO): 2.40–2.65 (4H, m); 2.75–2.95 (4H, m); 3.85–4.05 (2H, m); 4.60 (2H, d); 7.74 (2H, d); 7.92 (2H, d); 8.41 (1H, br.t); 11.42 (1H, s)

b) 3-(2,4-Dioxo-3,4,7,8-tetrahydro-2H-thiopyrano[4,3-d]pyrimidin-1(5H)-yl)-N-(2-oxo-2-[4-(2-pyrazinyl)phenyl]ethyl)propanecarboxamide Bis(triphenylphosphino)palladium(II) chloride (31 mg, 0.044 mmol) and 2-tributylstannylpyrazine (196 mg, 0.53 mmol) are added to a solution of the compound from Example 5a) (200 mg, 0.44 mmol) in DMF (5 ml). The reaction mixture is stirred at 120° C. overnight. After cooling and filtration, the reaction mixture is separated directly by preparative HPLC (column: Kromasil 100 C 18, 5 μm, 250×40 mm; mobile phase: acetonitrile/water; flow rate: 25 ml/min; UV detection at 210 nm). Following concentration under reduced pressure, 44 mg (22%) of the product are obtained as a colourless solid.

MS (DCI): 451.9 (M+H⁺)

¹H-NMR (d⁶-DMSO): 2.40–2.65 (4H, m); 2.80–2.95 (4H, m); 3.90–4.05 (2H, m); 4.68 (2H, d); 8.12 (2H, d); 8.32 (2H, d); 8.49 (1H, br.t); 8.70 (1H, m); 8.80 (1H, m); 9.37 (1H, m); 11.43 (1H, br.s)

The compounds listed in the table below were prepared in a similar manner:

| No. | Structure | Retention time R$_t$ [min] (HPLC method) | Mass [M + H]⁺ |
|---|---|---|---|
| 6 | 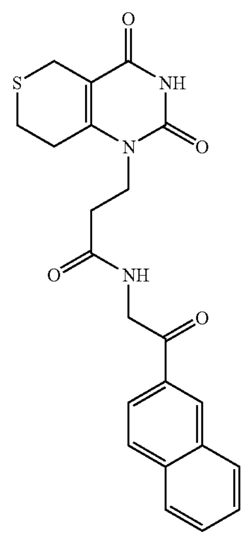 | 3.96 (A) | 441.1 [M + NH₄]⁺ |
| 7 | 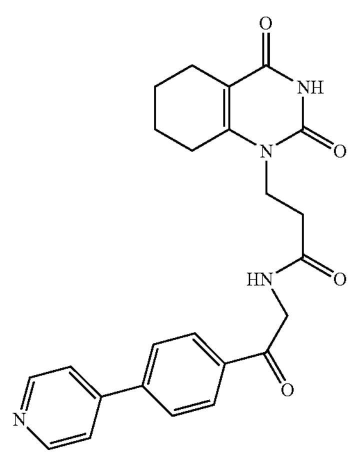 | 3.18 (A) | 433 |

-continued
| No. | Structure | Retention time $R_t$ [min] (HPLC method) | Mass $[M + H]^+$ |
|---|---|---|---|
| 8 | 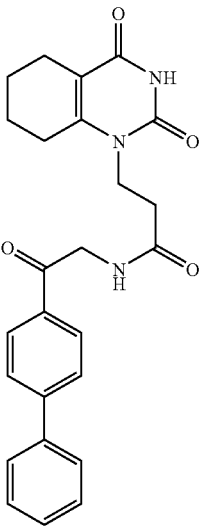 | 3.59 (C) | 432 |
| 9 | 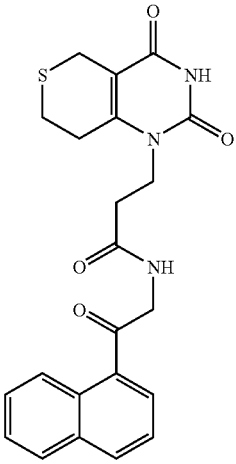 | 3.91 (A) | 441 $[M + NH_3]^+$ |
| 10 | 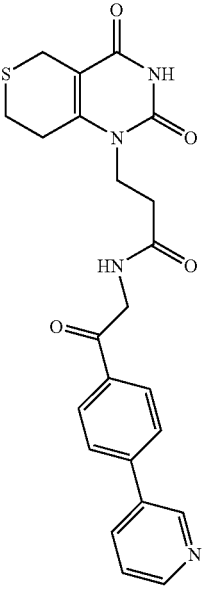 | 3.13 (A) | 451.2 |

-continued

| No. | Structure | Retention time R$_t$ [min] (HPLC method) | Mass [M + H]$^+$ |
|---|---|---|---|
| 11 | 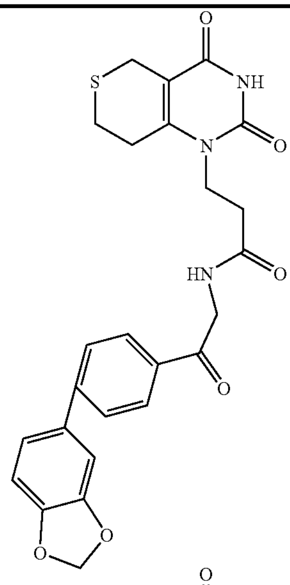 | 4.09 (A) | 476.3 |
| 12 | 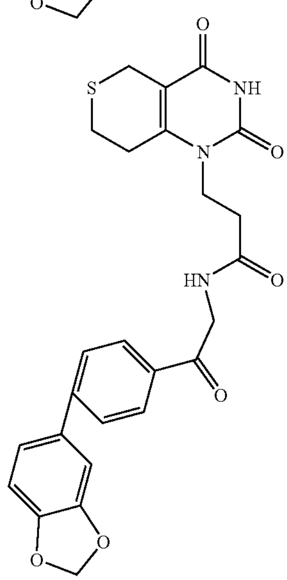 | 4.05 (A) | 494.4 |
| 13 | 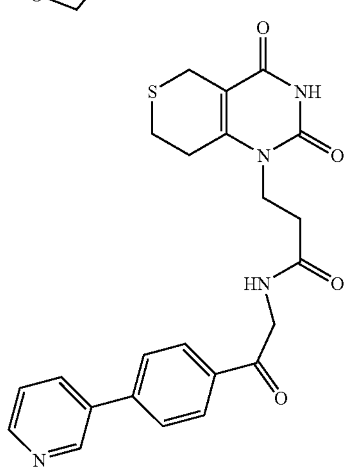 | 3.13 (A) | 451.4 |

-continued
| No. | Structure | Retention time $R_t$ [min] (HPLC method) | Mass [M + H]$^+$ |
|---|---|---|---|
| 14 | 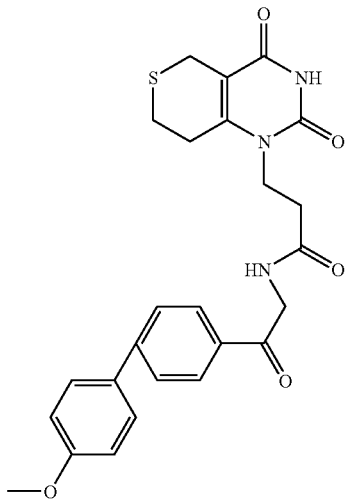 | 3.59 (B) | 480.2 |
| 15 | 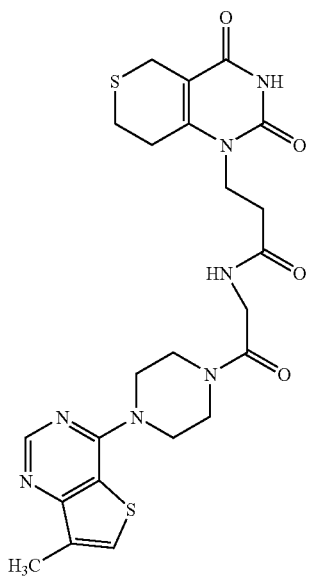 | 3.17 (A) | 530 |

-continued
| No. | Structure | Retention time $R_t$ [min] (HPLC method) | Mass $[M + H]^+$ |
|---|---|---|---|
| 16 | 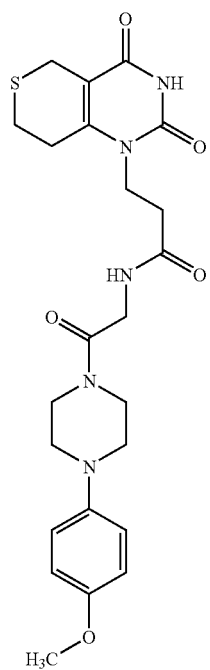 | 2.38 (C) | 488 |
| 17 | 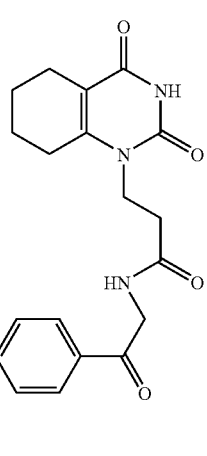 | 3.69 (B) | 462.4 |

-continued
| No. | Structure | Retention time $R_t$ [min] (HPLC method) | Mass $[M + H]^+$ |
|---|---|---|---|
| 18 | 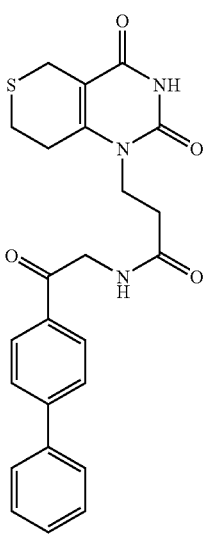 | 3.71 (B) | 450.4 |
| 19 | 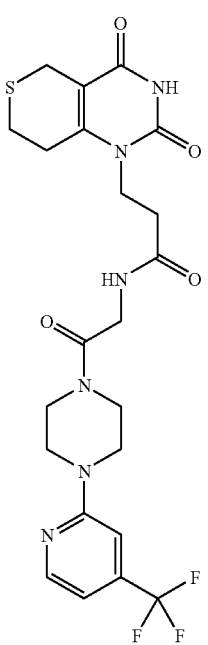 | 3.23 (B) | 527.3 |

| No. | Structure | Retention time R$_t$ [min] (HPLC method) | Mass [M + H]$^+$ |
|---|---|---|---|
| 20 | 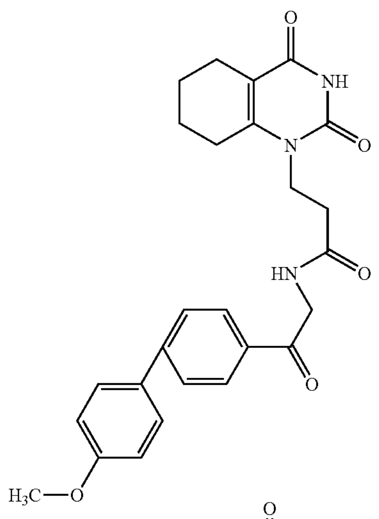 | 2.75 (B) | 447.4 |
| 21 | 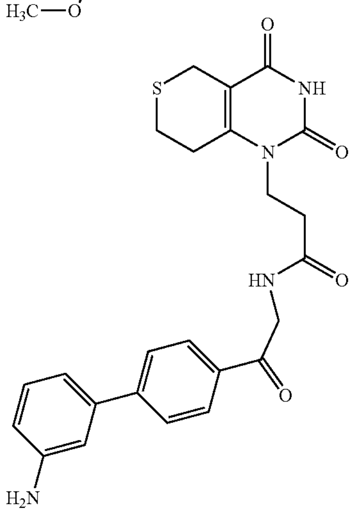 | 2.65 (B) | 465.2 |
| 22 | 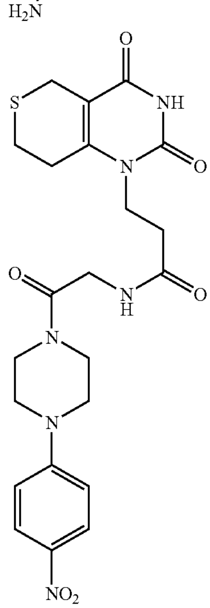 | 3.69 (A) | 520 [M + NH$_4$]$^+$ |

-continued

| No. | Structure | Retention time $R_t$ [min] (HPLC method) | Mass [M + H]$^+$ |
|---|---|---|---|
| 23 | 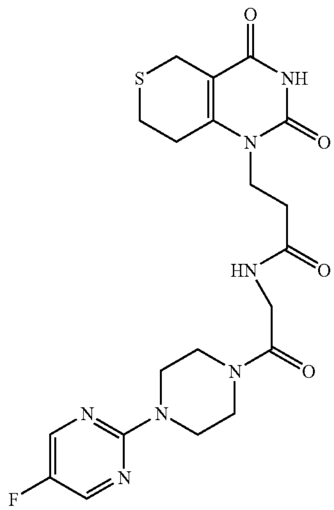 | 3.43 (A) | 478 |
| 24 | 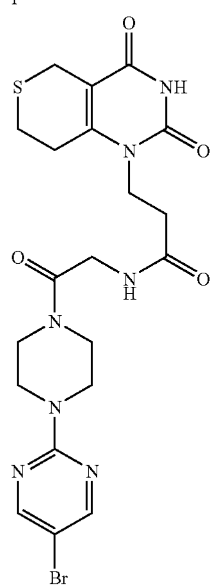 | 3.71 (A) | 538.1 |
| 25 | 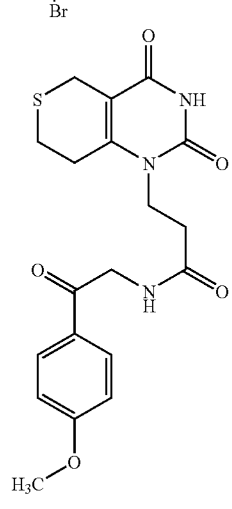 | 2.88 (C) | 404 |

-continued

| No. | Structure | Retention time $R_t$ [min] (HPLC method) | Mass [M + H]⁺ |
|---|---|---|---|
| 26 | 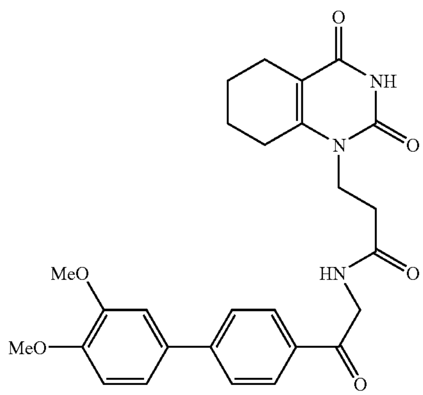 | 3.45 (B) | 492.4 |
| 27 | 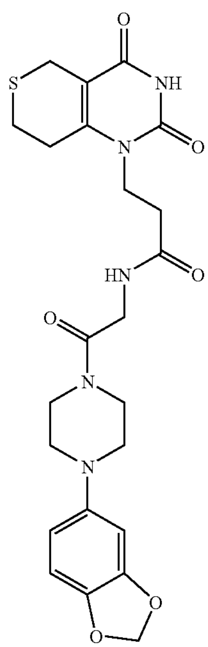 | 2.90 (B) | 502.4 |
| 28 | 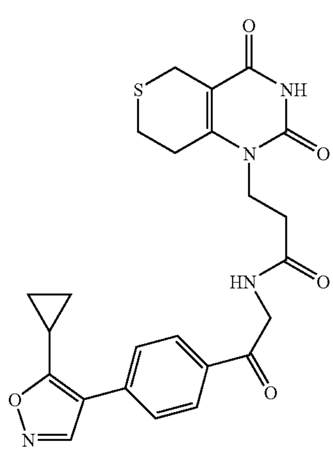 | 3.38 (B) | 481.3 |

-continued

| No. | Structure | Retention time $R_t$ [min] (HPLC method) | Mass $[M + H]^+$ |
|---|---|---|---|
| 29 | 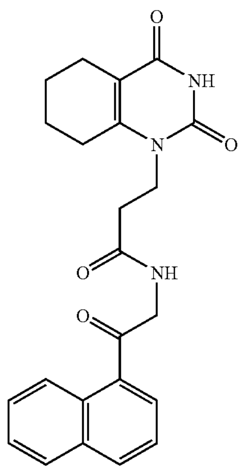 | 3.95 (A) | 406 |
| 30 | 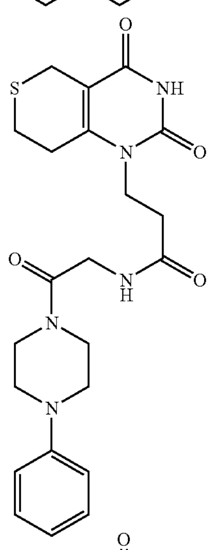 | 2.99 (B) | 458.4 |
| 31 | 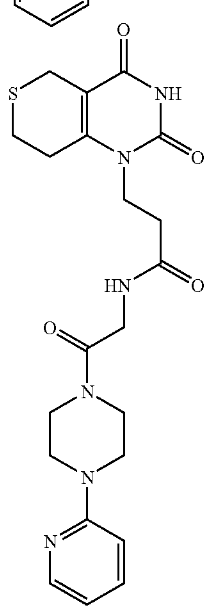 | 2.98 (A) | 459 |

| No. | Structure | Retention time $R_t$ [min] (HPLC method) | Mass $[M + H]^+$ |
|---|---|---|---|
| 32 | 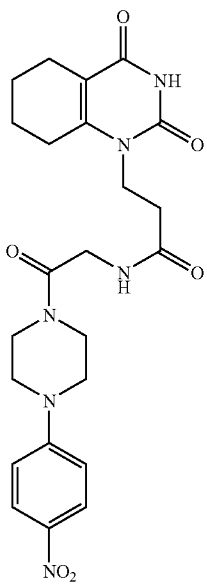 | 3.71 (A) | 485.5 |
| 33 | 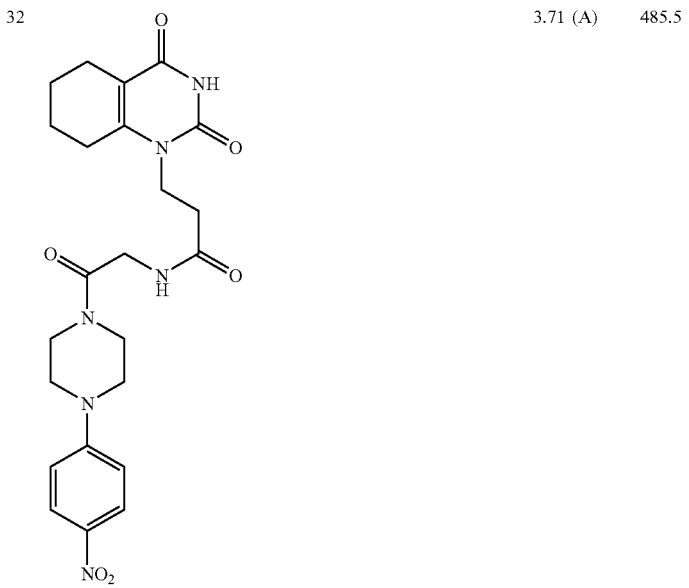 | 3.00 (A) | 460.2 |

-continued
| No. | Structure | Retention time $R_t$ [min] (HPLC method) | Mass $[M + H]^+$ |
|---|---|---|---|
| 34 | 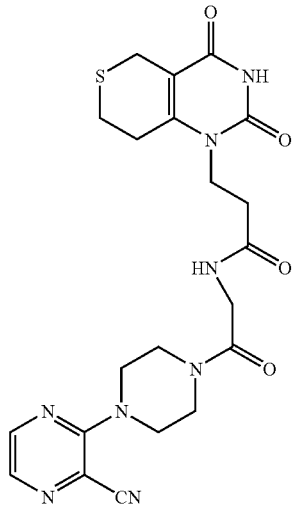 | 3.37 (A) | 485 |
| 35 | 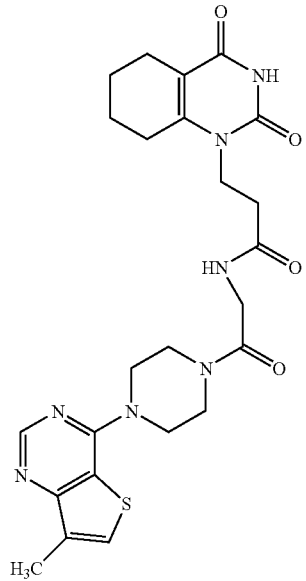 | 3.21 (A) | 512 |

-continued
| No. | Structure | Retention time $R_t$ [min] (HPLC method) | Mass $[M + H]^+$ |
|---|---|---|---|
| 36 | 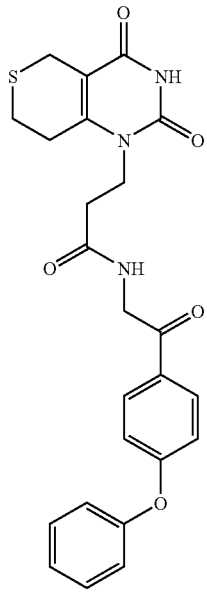 | 3.69 (B) | 466.3 |
| 37 | 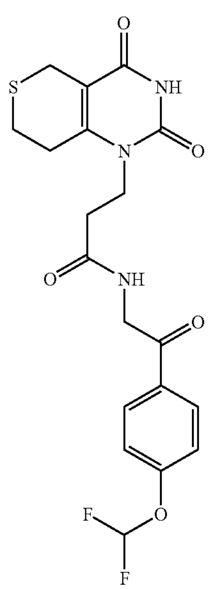 | 2.16 (C) | 440 |

-continued
| No. | Structure | Retention time $R_t$ [min] (HPLC method) | Mass $[M + H]^+$ |
|---|---|---|---|
| 38 | 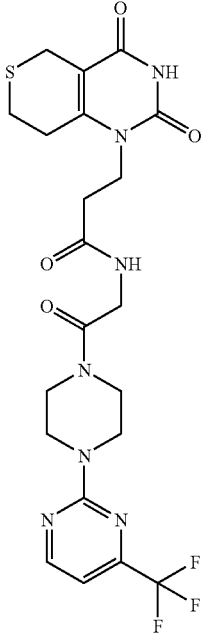 | 3.87 (A) | 545.2 $[M + NH_4]^+$ |
| 39 | 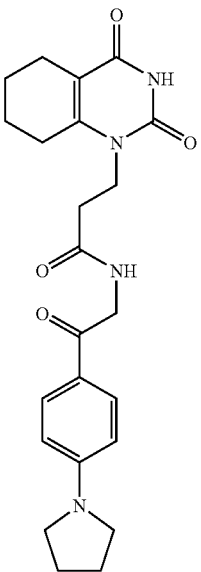 | 3.97 (A) | 425.4 |

-continued

| No. | Structure | Retention time $R_t$ [min] (HPLC method) | Mass [M + H]+ |
|---|---|---|---|
| 40 | 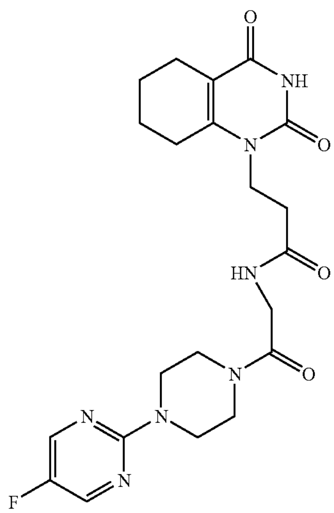 | 3.47 (A) | 460 |
| 41 | 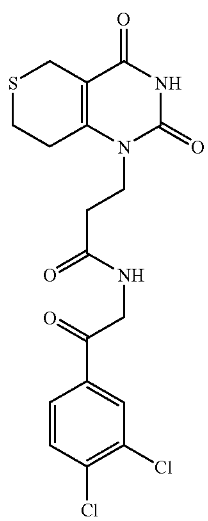 | 4.01 (A) | 459.1 [M + NH$_4$]+ |
| 42 | 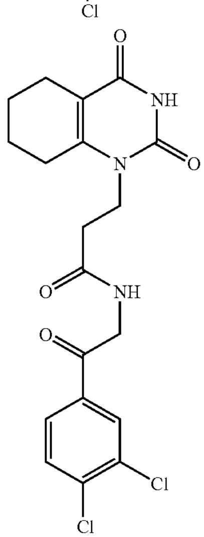 | 4.02 (A) | 424 |

-continued

| No. | Structure | Retention time $R_t$ [min] (HPLC method) | Mass $[M + H]^+$ |
|---|---|---|---|
| 43 | 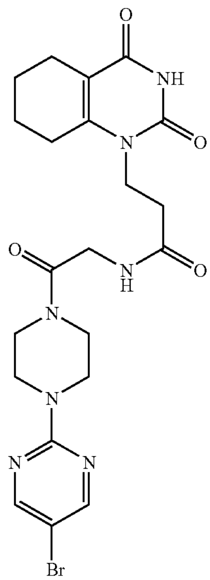 | 3.73 (A) | 520 |
| 44 | 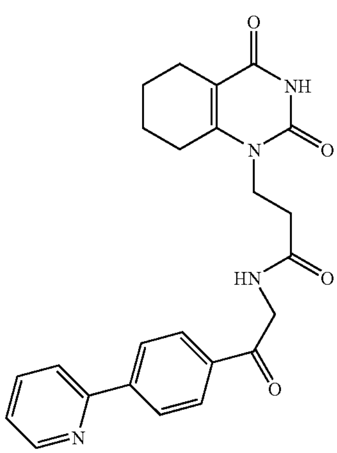 | 2.78 (B) | 433.4 |

| No. | Structure | Retention time $R_t$ [min] (HPLC method) | Mass $[M + H]^+$ |
|---|---|---|---|
| 45 | 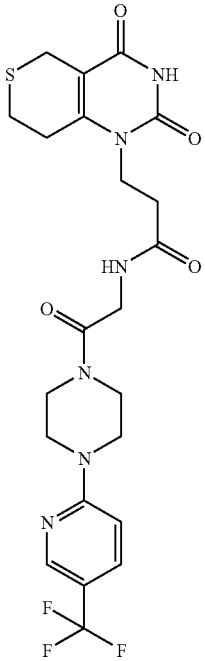 | 3.36 (A) | 527 |
| 46 | 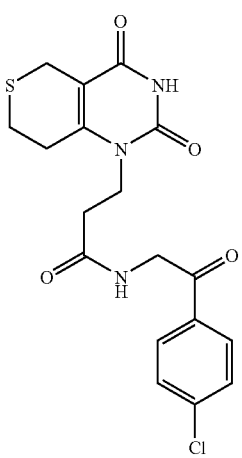 | 3.80 (A) | 430.2 $[M + Na]^+$ |

-continued

| No. | Structure | Retention time $R_t$ [min] (HPLC method) | Mass [M + H]$^+$ |
|---|---|---|---|
| 47 | 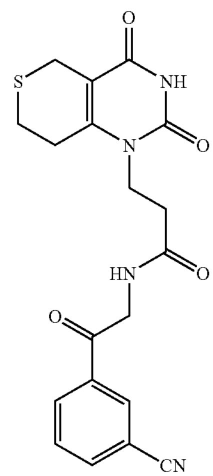 | 2.86 (B) | 399.4 |
| 48 | 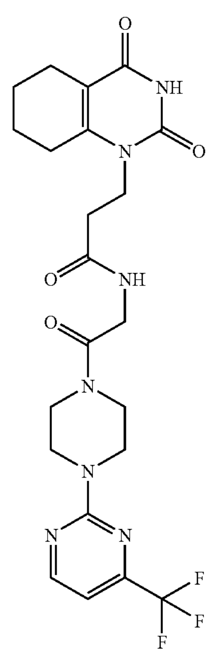 | 3.93 (A) | 510.4 |

-continued

| No. | Structure | Retention time $R_t$ [min] (HPLC method) | Mass $[M + H]^+$ |
|---|---|---|---|
| 49 | 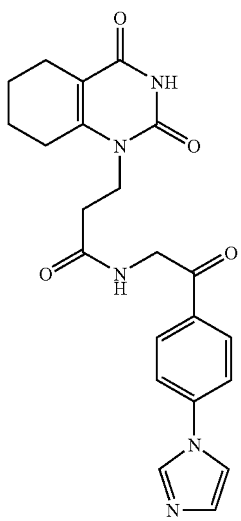 | 3.10 (A) | 422.1 |
| 50 | 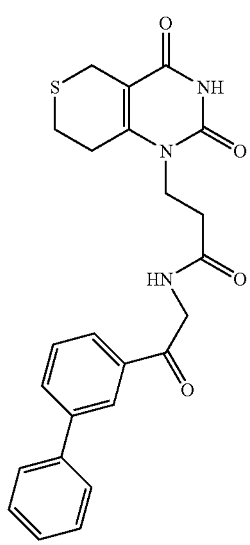 | 3.64 (B) | 432.3 |

-continued

| No. | Structure | Retention time R$_t$ [min] (HPLC method) | Mass [M + H]$^+$ |
|---|---|---|---|
| 51 | 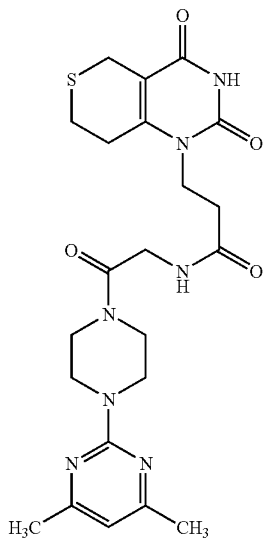 | 3.16 (A) | 488 |
| 52 | 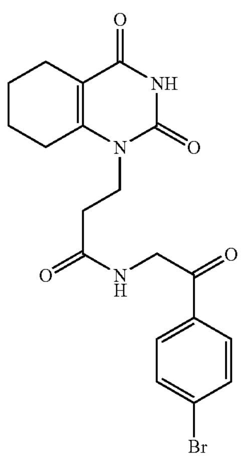 | 3.89 (A) | 434 |
| 53 | 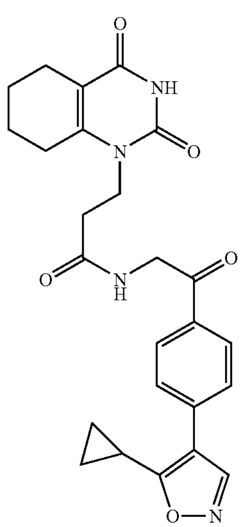 | 3.47 (B) | 463.4 |

-continued
| No. | Structure | Retention time $R_t$ [min] (HPLC method) | Mass $[M + H]^+$ |
|---|---|---|---|
| 54 | 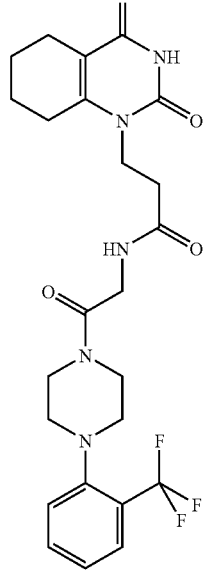 | 4.06 (A) | 508.3 |
| 55 | 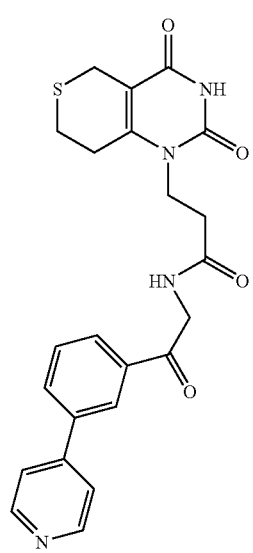 | 3.18 (A) | 451.4 |

-continued
| No. | Structure | Retention time $R_t$ [min] (HPLC method) | Mass $[M + H]^+$ |
|---|---|---|---|
| 56 | 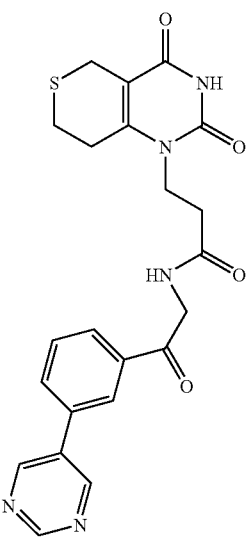 | 2.65 (B) | 452.3 |
| 57 | 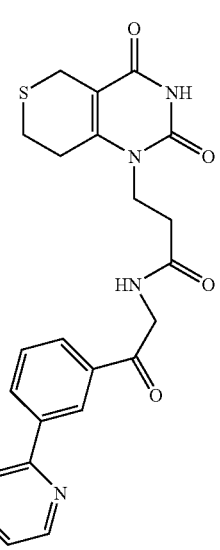 | 2.57 (B) | 451.3 |

-continued

| No. | Structure | Retention time $R_t$ [min] (HPLC method) | Mass [M + H]⁺ |
|---|---|---|---|
| 58 | 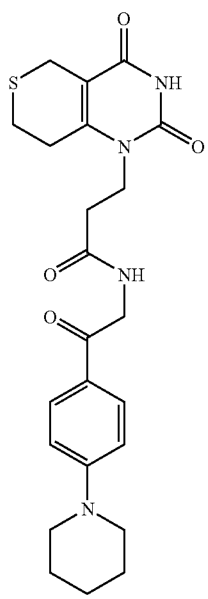 | 3.31 (A) | 457 |
| 59 | 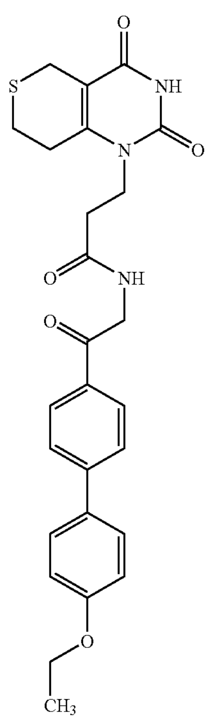 | 4.33 (A) | 511.3 [M + NH₄]⁺ |

-continued
| No. | Structure | Retention time $R_t$ [min] (HPLC method) | Mass [M + H]⁺ |
|---|---|---|---|
| 60 | 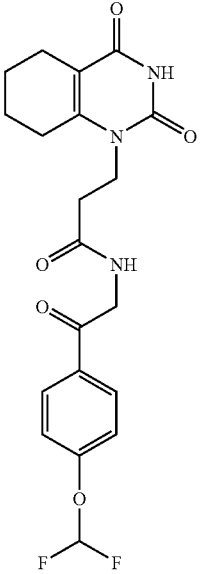 | 3.39 (C) | 422 |
| 61 | 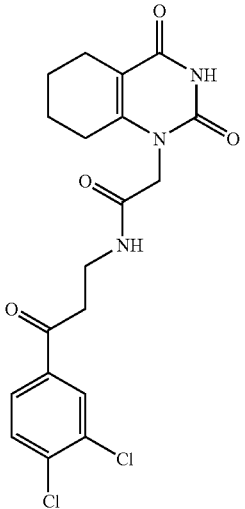 | 4.04 (A) | 441 [M + NH₄]⁺ |

-continued

| No. | Structure | Retention time R_t [min] (HPLC method) | Mass [M + H]+ |
|-----|-----------|----------------------------------------|---------------|
| 62  | 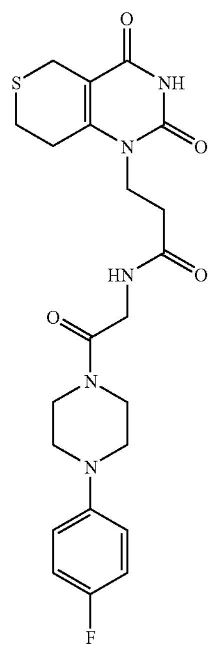          | 3.13 (B)                               | 476.5         |
| 63  | 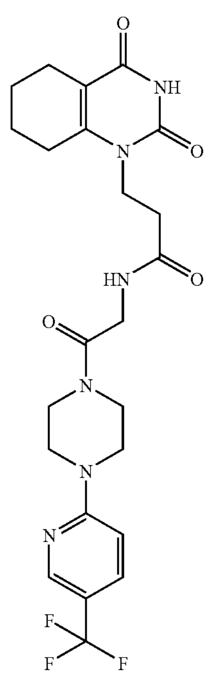          | 3.39 (A)                               | 509           |

-continued
| No. | Structure | Retention time $R_t$ [min] (HPLC method) | Mass $[M + H]^+$ |
|---|---|---|---|
| 64 | 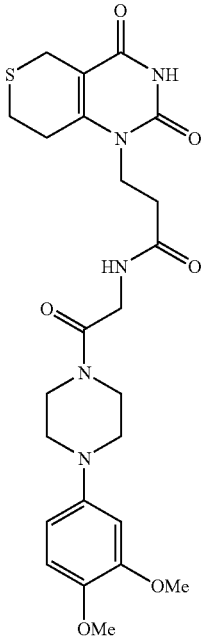 | 3.39 (A) | 527.1 |
| 65 | 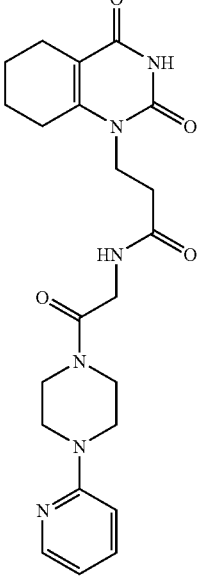 | 3.02 (A) | 441.4 |

-continued
| No. | Structure | Retention time $R_t$ [min] (HPLC method) | Mass $[M + H]^+$ |
|---|---|---|---|
| 66 | 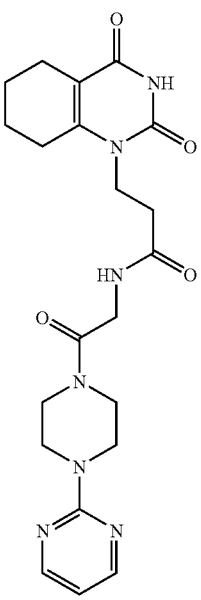 | 3.05 (A) | 442.4 |
| 67 | 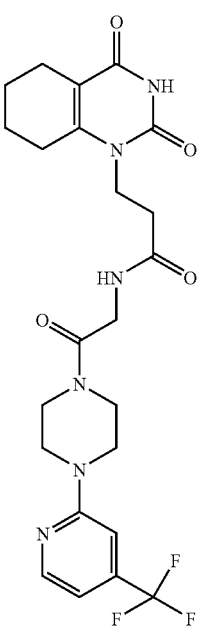 | 3.32 (B) | 509.4 |

-continued
| No. | Structure | Retention time $R_t$ [min] (HPLC method) | Mass $[M + H]^+$ |
|---|---|---|---|
| 68 | 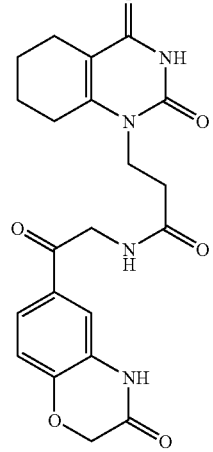 | 3.33 (A) | 427.3 |
| 69 | 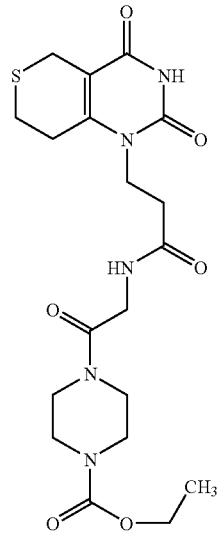 | 2.62 (B) | 454.4 |

| No. | Structure | Retention time $R_t$ [min] (HPLC method) | Mass [M + H]+ |
|---|---|---|---|
| 70 | 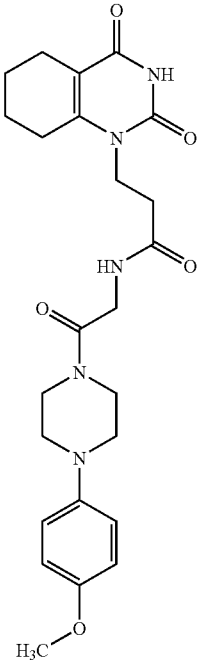 | 2.70 (B) | 470.3 |
| 71 | 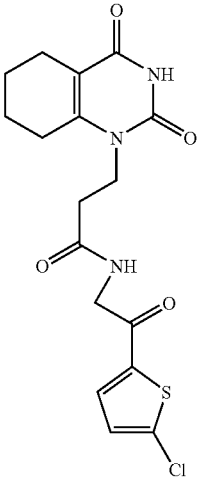 | 3.76 (A) | 413.1 [M + NH$_4$]+ |

|     |           | -continued |             |
| --- | --------- | ---------- | ----------- |
| No. | Structure | Retention time $R_t$ [min] (HPLC method) | Mass $[M + H]^+$ |
| 72  |           | 3.82 (A)   | 390.6       |
| 73  |           | 3.67 (A)   | 411.4       |
| 74  |           | 3.06 (B)   | 440.4       |

-continued

| No. | Structure | Retention time R_t [min] (HPLC method) | Mass [M + H]+ |
|---|---|---|---|
| 75 | 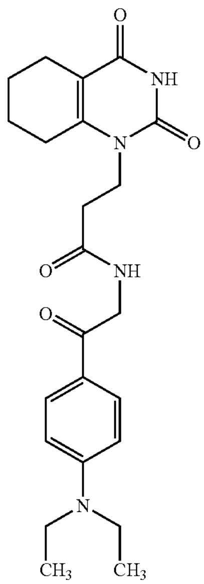 | 3.42 (A) | 427 |
| 76 | 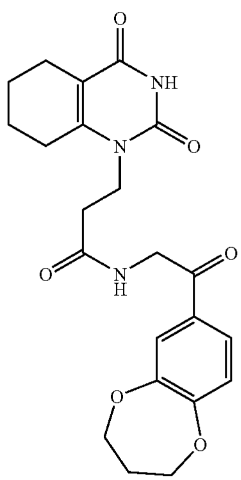 | 3.66 (A) | 428.4 |
| 77 | 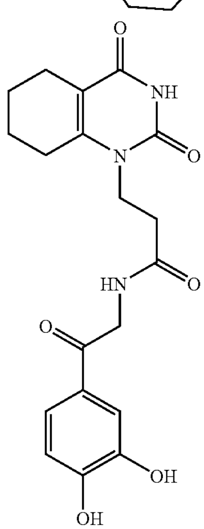 | 2.35 (C) | 388 |

-continued
| No. | Structure | Retention time $R_t$ [min] (HPLC method) | Mass $[M + H]^+$ |
|---|---|---|---|
| 78 | 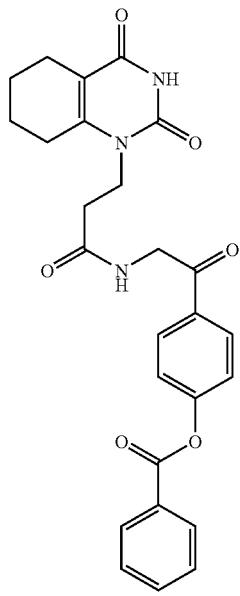 | 4.19 (A) | 476.4 |
| 79 | 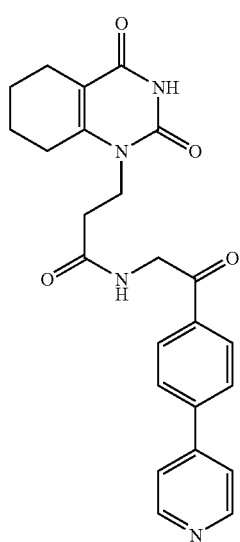 | 2.11 (B) | 433.4 |

| No. | Structure | Retention time $R_t$ [min] (HPLC method) | Mass $[M + H]^+$ |
|---|---|---|---|
| 80 | 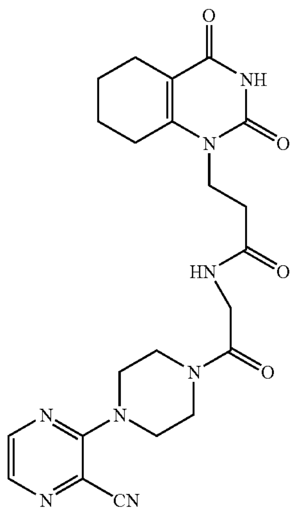 | 3.40 (A) | 467 |
| 81 | 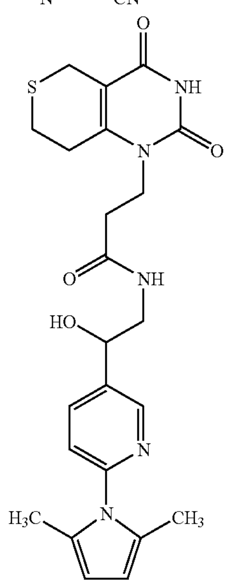 | 2.02 (C) | 470 |
| 82 | 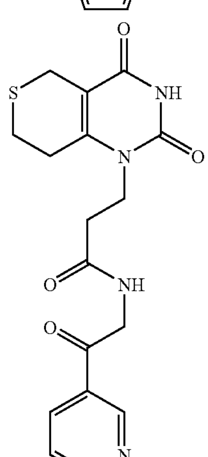 | 2.85 (A) | 375.1 |

-continued

| No. | Structure | Retention time R_t [min] (HPLC method) | Mass [M + H]+ |
|---|---|---|---|
| 83 | 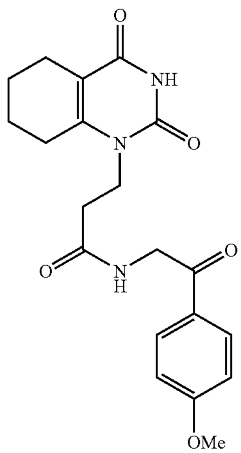 | 3.63 (A) | 408.3 [M + N9]+ |
| 84 | 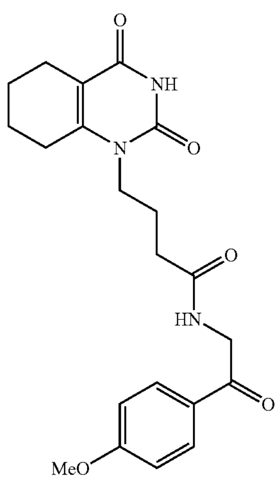 | 3.66 (A) | 400.1 |
| 85 | 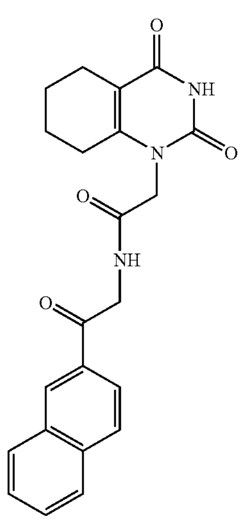 | 3.66 (C) | 392.4 |

-continued

| No. | Structure | Retention time R$_t$ [min] (HPLC method) | Mass [M + H]$^+$ |
|---|---|---|---|
| 86 | 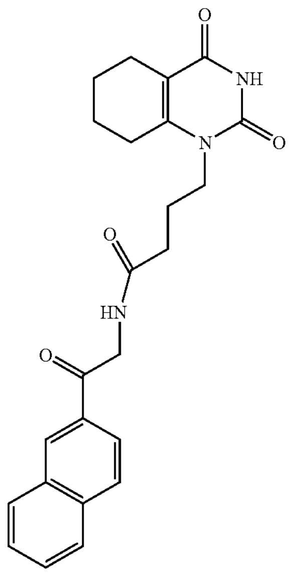 | 3.98 (A) | 420 |
| 87 | 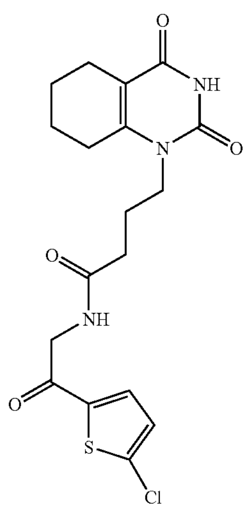 | 3.42 (C) | 410 |
| 88 | 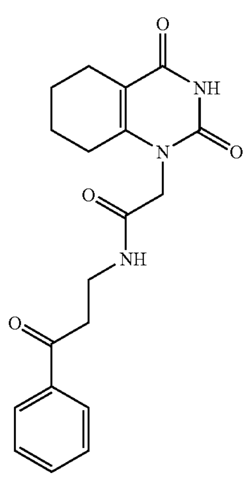 | 3.60 (A) | 378.5 [M + Na]$^+$ |

-continued
| No. | Structure | Retention time $R_t$ [min] (HPLC method) | Mass [M + H]$^+$ |
|---|---|---|---|
| 89 | 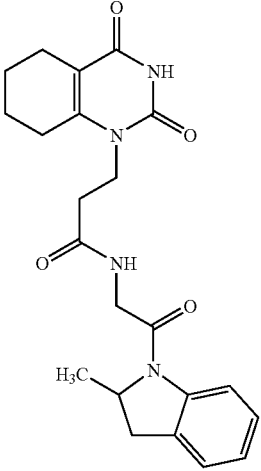 | 3.80 (A) | 411.4 |
| 90 | 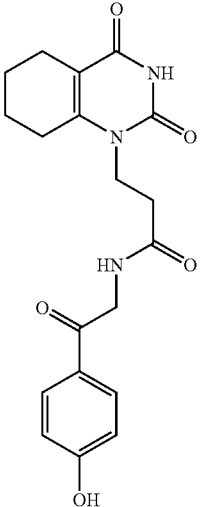 | 3.29 (A) | 372 |
| 91 | 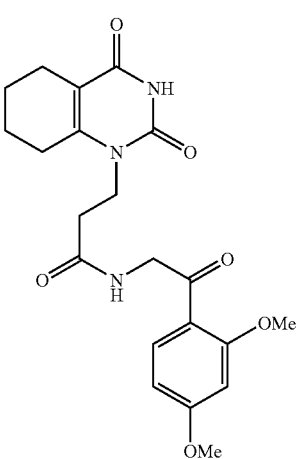 | 3.14 (B) | 416.4 |

-continued
| No. | Structure | Retention time R_t [min] (HPLC method) | Mass [M + H]+ |
|---|---|---|---|
| 92 | 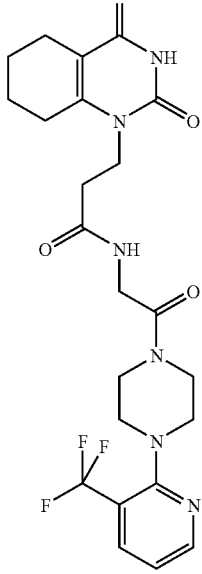 | 3.67 (A) | 509.4 |
| 93 | 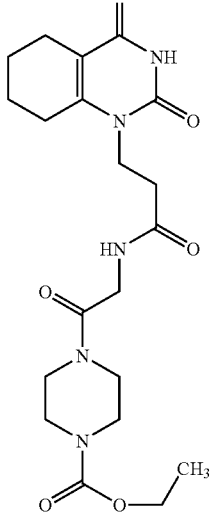 | 2.66 (B) | 436.5 |

-continued
| No. | Structure | Retention time $R_t$ [min] (HPLC method) | Mass $[M + H]^+$ |
|---|---|---|---|
| 94 | 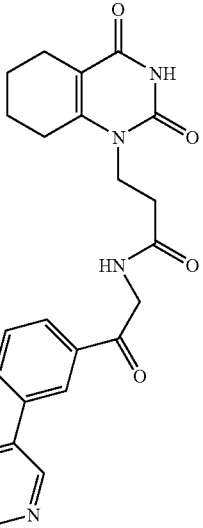 | 2.94 (C) | 434.4 |
| 95 | 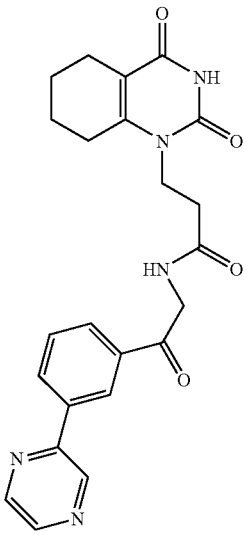 | 2.68 (B) | 434.3 |
| 96 | 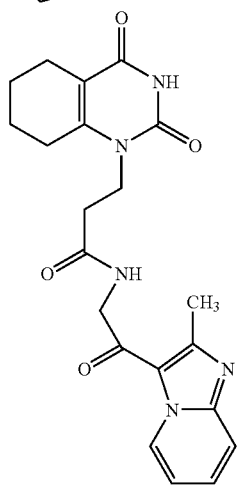 | 3.07 (A) | 410.2 |

-continued
| No. | Structure | Retention time $R_t$ [min] (HPLC method) | Mass [M + H]$^+$ |
|---|---|---|---|
| 97 | 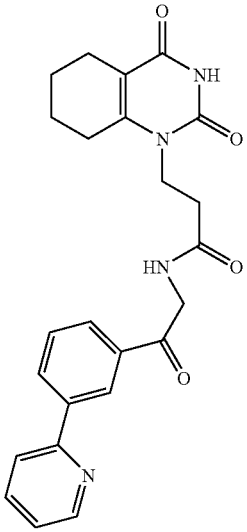 | 2.63 (b) | 433.3 |
| 98 | 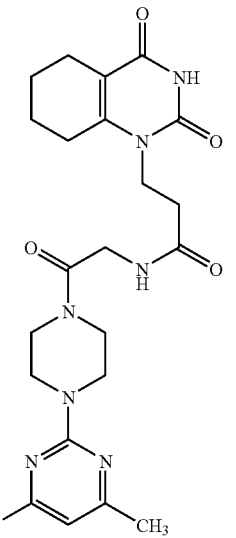 | 3.19 (A) | 470 |

-continued
| No. | Structure | Retention time $R_t$ [min] (HPLC method) | Mass [M + H]$^+$ |
|---|---|---|---|
| 99 | 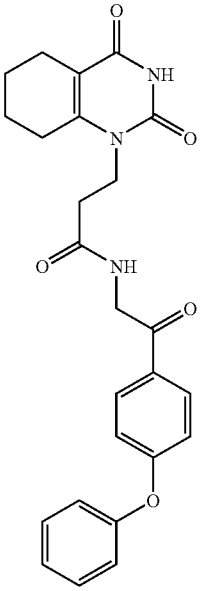 | 3.71 (B) | 448.3 |
| 100 | 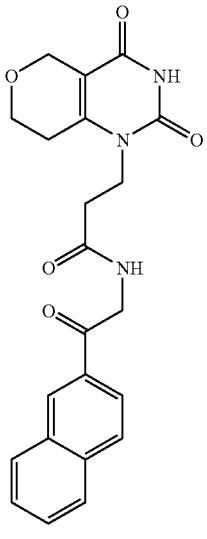 | 3.72 (A) | 430 [M + Na]$^+$ |

-continued

| No. | Structure | Retention time R$_t$ [min] (HPLC method) | Mass [M + H]$^+$ |
|---|---|---|---|
| 101 | 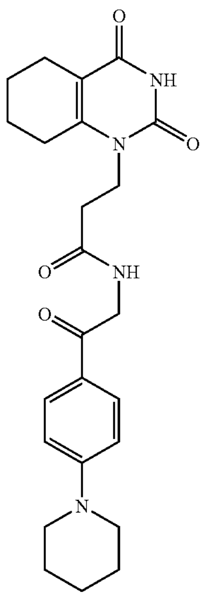 | 3.35 (A) | 439 |
| 102 | 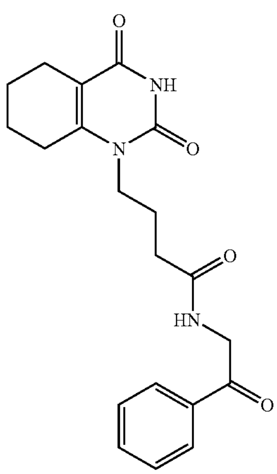 | 3.61 (A) | 392.2 [M + Na]$^+$ |
| 103 | 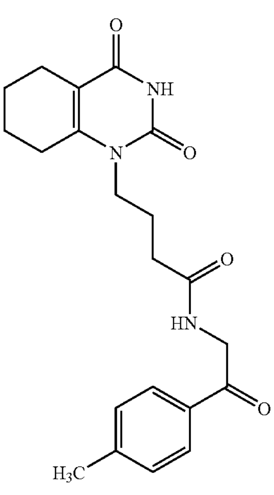 | 3.43 (C) | 406.3 [M + Na]$^+$ |

-continued

| No. | Structure | Retention time $R_t$ [min] (HPLC method) | Mass [M + H]⁺ |
|---|---|---|---|
| 104 | 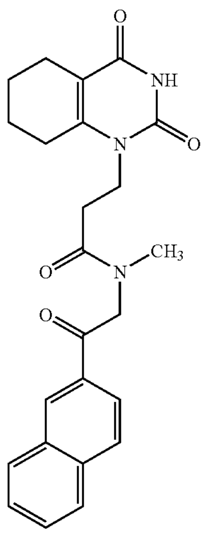 | 4.04 (A) | 437.1 [M + NH₄]⁺ |
| 105 | 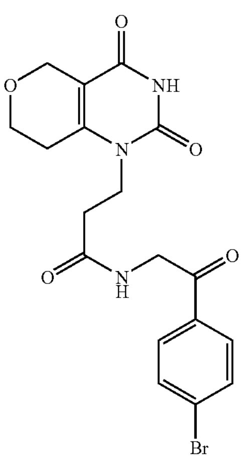 | 3.38 (A) | 453 [M + NH₄]⁺ |
| 106 | 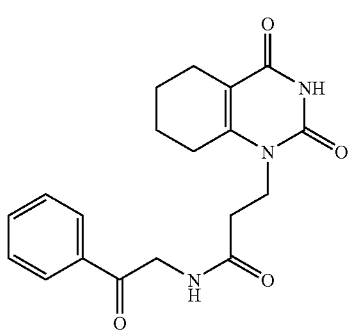 | 3.11 (C) | 356 |

-continued
| No. | Structure | Retention time $R_t$ [min] (HPLC method) | Mass [M + H]+ |
|---|---|---|---|
| 107 | 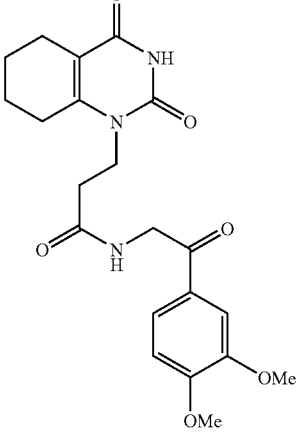 | 2.79 (B) | 416.2 |
| 108 | 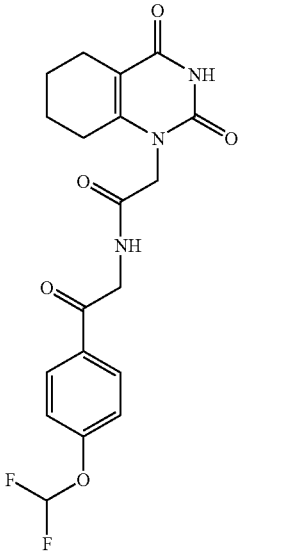 | 3.39 (C) | 408 |
| 109 | 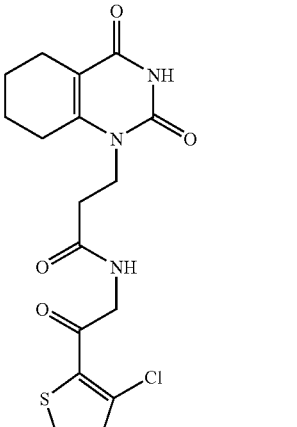 | 4.22 (A) | 418.3 [M + Na]+ |

-continued

| No. | Structure | Retention time R_t [min] (HPLC method) | Mass [M + H]+ |
|---|---|---|---|
| 110 | 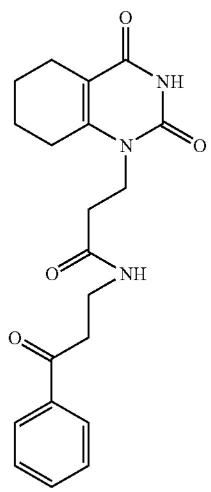 | 3.59 (A) | 392.4 [M + Na]+ |
| 111 | 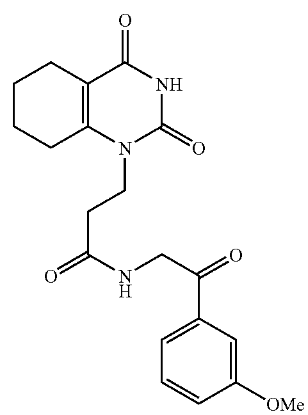 | 2.94 (C) | 386 |
| 112 | 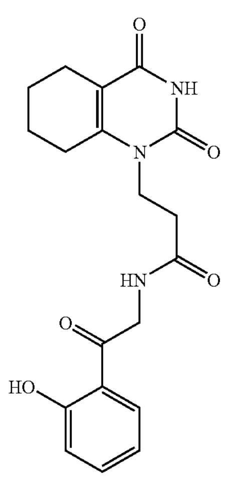 | 2.89 (C) | 372 |

| No. | Structure | Retention time R$_t$ [min] (HPLC method) | Mass [M + H]$^+$ |
|---|---|---|---|
| 113 | 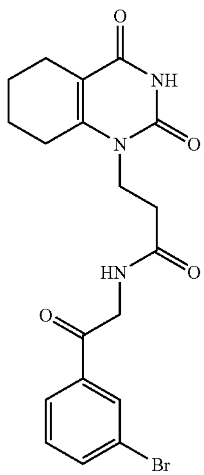 | 3.24 (B) | 436.1 |
| 114 | 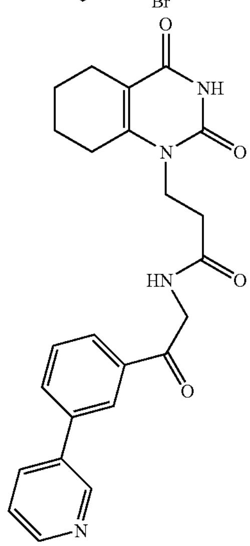 | 2.36 (B) | 433.4 |
| 115 | 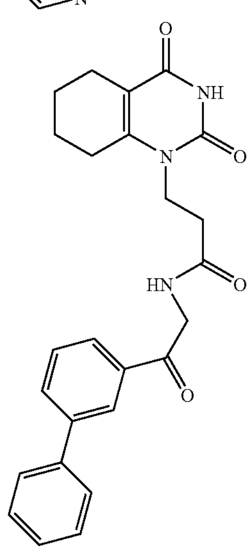 | 3.61 (B) | 450.3 |

-continued

| No. | Structure | Retention time R$_t$ [min] (HPLC method) | Mass [M + H]$^+$ |
|-----|-----------|------------------------------------------|------------------|
| 116 | 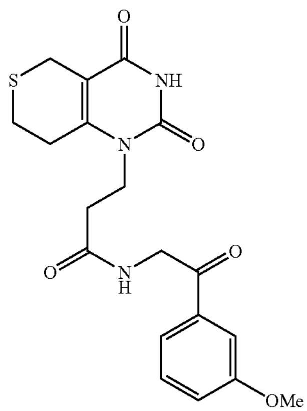 | 3.12 (A) | 423.3 [M + NH$_4$]$^+$ |
| 117 | 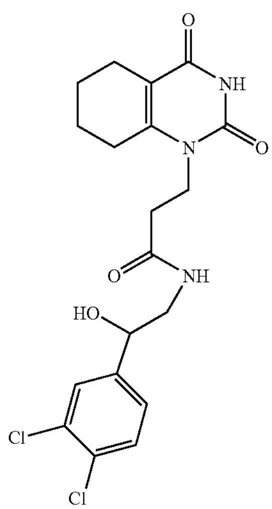 | 3.84 (A) | 443.2 [M + NH$_4$]$^+$ |
| 118 | 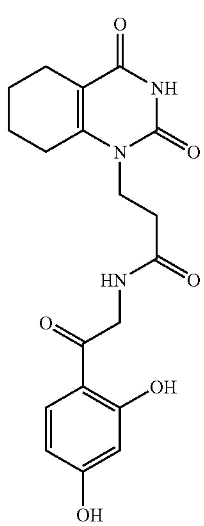 | 2.57 (B) | 388.2 |

-continued
| No. | Structure | Retention time $R_t$ [min] (HPLC method) | Mass $[M + H]^+$ |
|---|---|---|---|
| 119 | 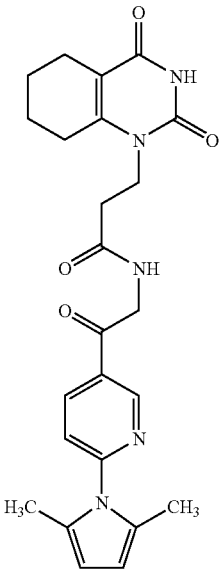 | 2.29 (C) | 450 |
| 120 | 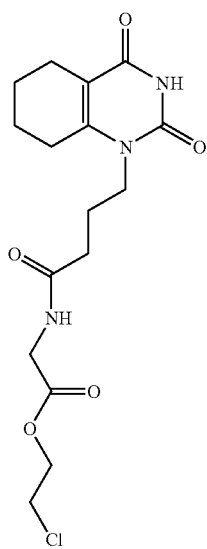 | 2.86 (C) | 372 |

| No. | Structure | Retention time $R_t$ [min] (HPLC method) | Mass $[M + H]^+$ |
|---|---|---|---|
| 121 | 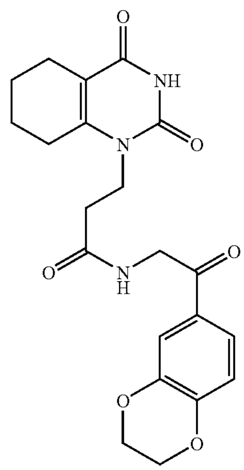 | 3.58 (A) | 414.1 |
| 122 | 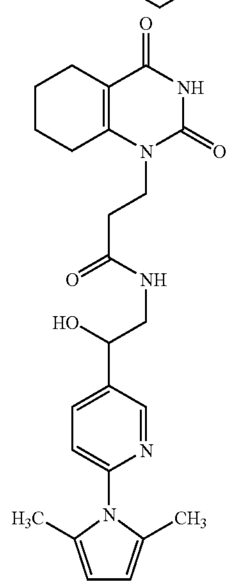 | 2.11 (C) | 452 |
| 123 | 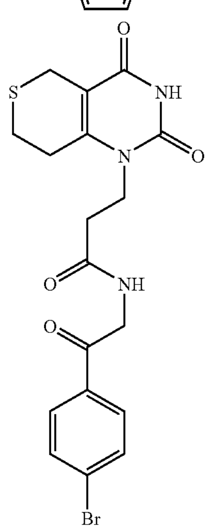 | 3.86 (A) | 452 |

-continued
| No. | Structure | Retention time $R_t$ [min] (HPLC method) | Mass $[M + H]^+$ |
|---|---|---|---|
| 124 | 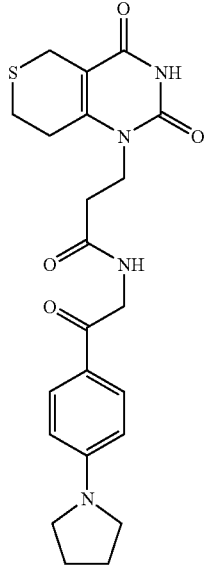 | 3.91 (A) | 443.4 |
| 125 | 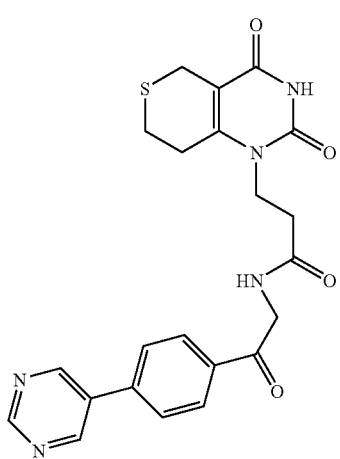 | 3.32 (A) | 452.1 |

-continued
| No. | Structure | Retention time $R_t$ [min] (HPLC method) | Mass [M + H]+ |
|---|---|---|---|
| 126 | 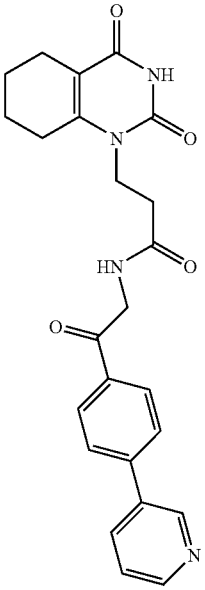 | 3.18 (A) | 433.5 |
| 127 | 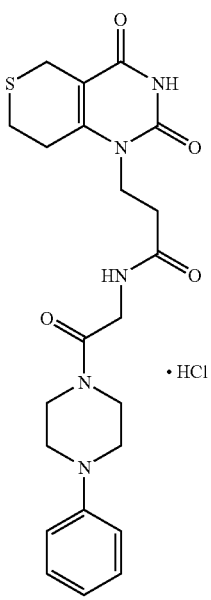 | 3.08 (B) | 458.3 |

-continued
| No. | Structure | Retention time $R_t$ [min] (HPLC method) | Mass [M + H]$^+$ |
|---|---|---|---|
| 128 | 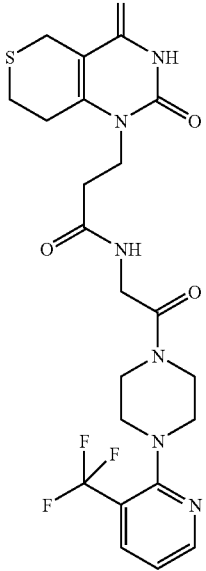 | 3.09 (C) | 527 |
| 129 | 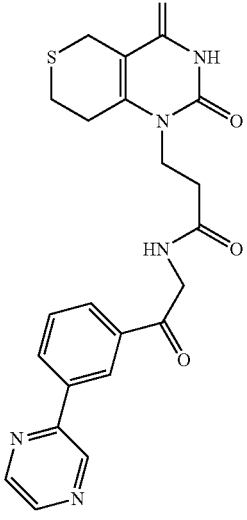 | 2.80 (B) | 452.2 |

|No.|Structure|Retention time R_t [min] (HPLC method)|Mass [M + H]+|
|---|---|---|---|
|130| 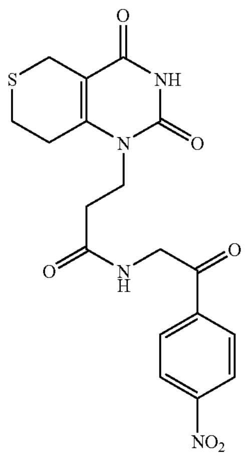 |2.98 (C)|419|
|131| 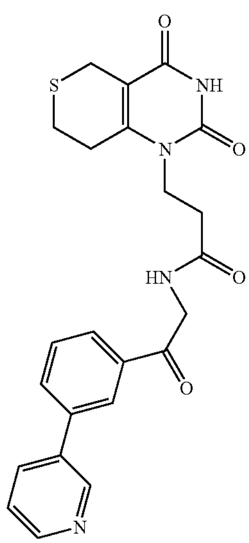 |2.16 (B)|451.2|
|132| 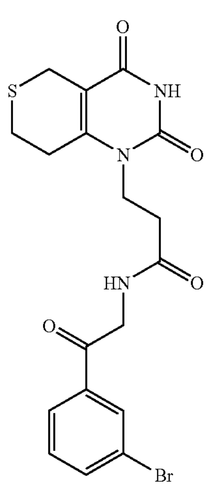 |3.85 (A)|468.9 [M + NH_4]+|

-continued

| No. | Structure | Retention time $R_t$ [min] (HPLC method) | Mass $[M + H]^+$ |
|---|---|---|---|
| 133 | 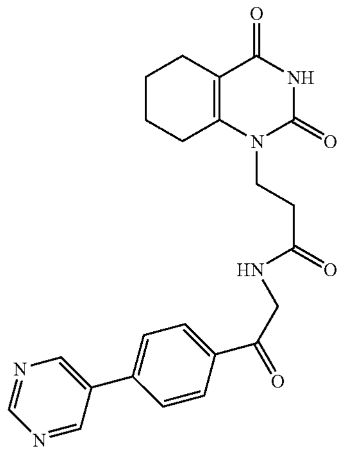 | 3.36 (A) | 434.1 |
| 134 | 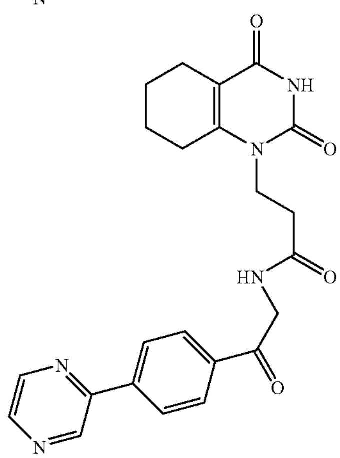 | 3.50 (A) | 434.3 |
| 135 | 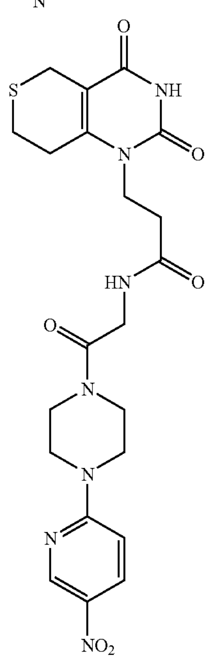 | 2.94 (B) | 504.3 |

-continued

| No. | Structure | Retention time R$_t$ [min] (HPLC method) | Mass [M + H]$^+$ |
|---|---|---|---|
| 136 | 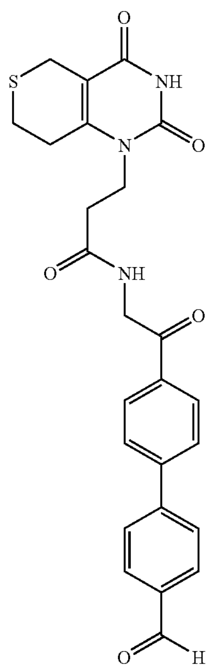 | 3.91 (A) | 495.5 [M + NH$_4$]$^+$ |
| 137 | 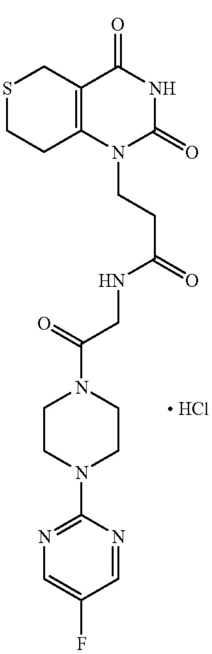 | 2.86 (B) | 478.3 |

-continued

| No. | Structure | Retention time R_t [min] (HPLC method) | Mass [M + H]+ |
|---|---|---|---|
| 138 | 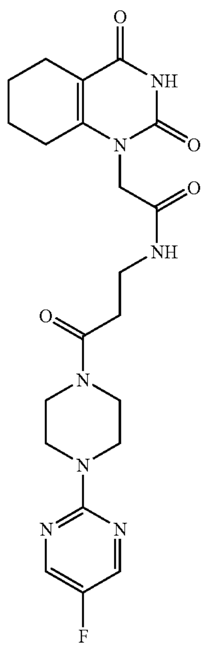 | 2.80 (B) | 478.3 |
| 139 | 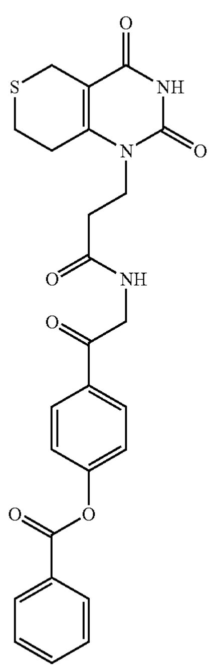 | 2.49 (C) | 494 |

-continued
| No. | Structure | Retention time $R_t$ [min] (HPLC method) | Mass $[M + H]^+$ |
|---|---|---|---|
| 140 | 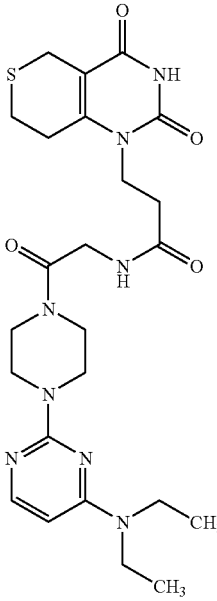 | 2.27 (B) | 531.3 |
| 141 | 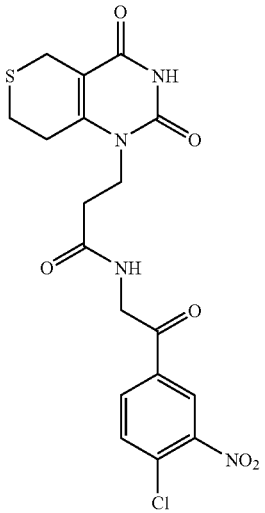 | 3.82 (A) | 453 |

-continued
| No. | Structure | Retention time $R_t$ [min] (HPLC method) | Mass $[M + H]^+$ |
|---|---|---|---|
| 142 | 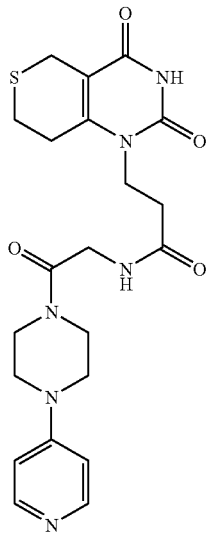 | 3.04 (A) | 459.2 |
| 143 | 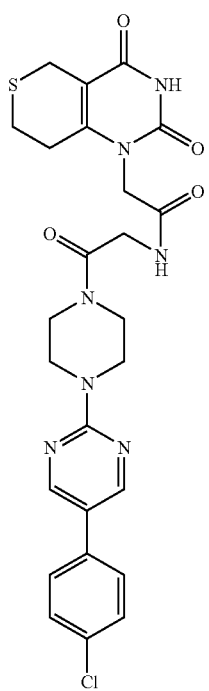 | 3.67 (B) | 556.2 |

| No. | Structure | Retention time $R_t$ [min] (HPLC method) | Mass [M + H]+ |
|---|---|---|---|
| 144 | 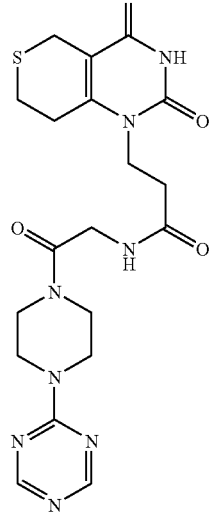 | 1.95 (B) | 461.2 |
| 145 | 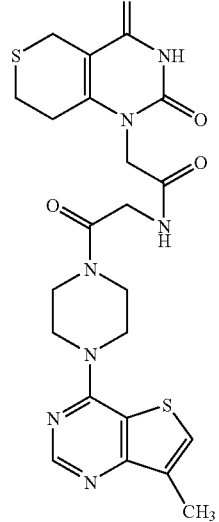 | 1.62 (B) | 516.2 |

| No. | Structure | Retention time $R_t$ [min] (HPLC method) | Mass [M + H]⁺ |
|---|---|---|---|
| 146 | 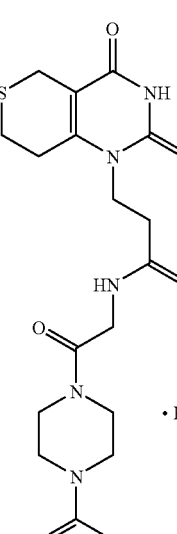 · HCl | 3.17 (A) | 459.2 |
| 147 | 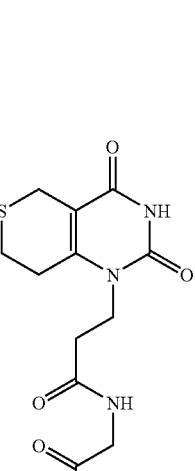 | 3.81 (A) | 497 |

-continued
| No. | Structure | Retention time R$_t$ [min] (HPLC method) | Mass [M + H]$^+$ |
|---|---|---|---|
| 148 | 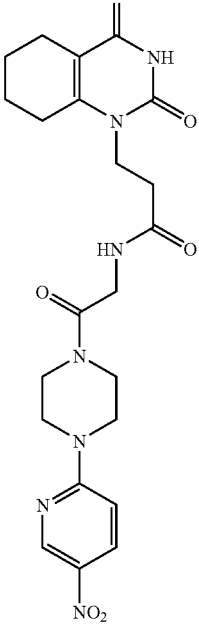 | 2.96 (B) | 486.3 |
| 149 | 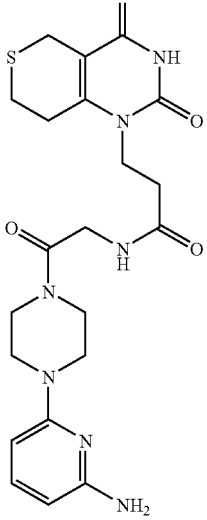 | 0.28 (B) | 474.1 |

-continued
| No. | Structure | Retention time R_t [min] (HPLC method) | Mass [M + H]+ |
|---|---|---|---|
| 150 | 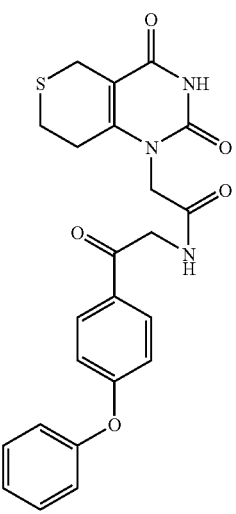 | 3.61 (B) | 452.1 |
| 151 | 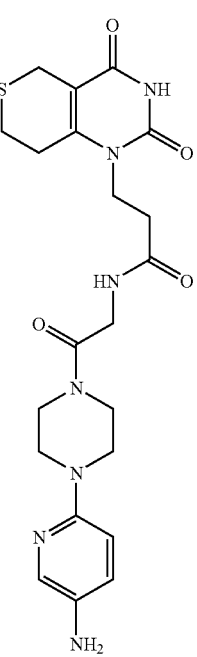 | 0.44 (B) | 474 |

-continued
| No. | Structure | Retention time $R_t$ [min] (HPLC method) | Mass $[M + H]^+$ |
|---|---|---|---|
| 152 | 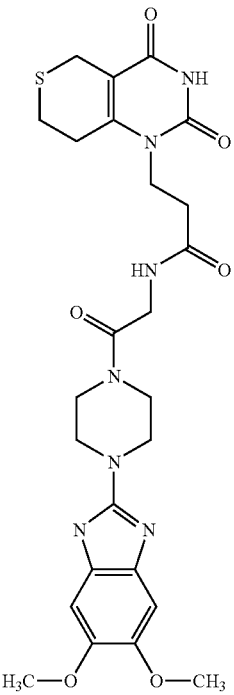 | 1.95 (B) | 558.2 |
| 153 | 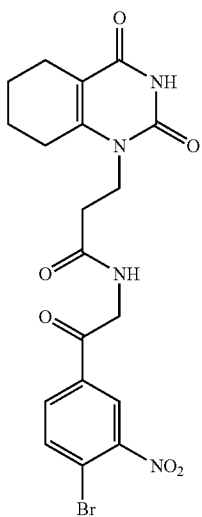 | 2.24 (C) | 479 |

-continued
| No. | Structure | Retention time $R_t$ [min] (HPLC method) | Mass [M + H]+ |
|---|---|---|---|
| 154 | 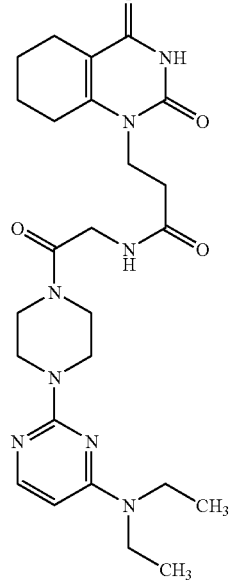 | 2.31 (B) | 513.3 |
| 155 | 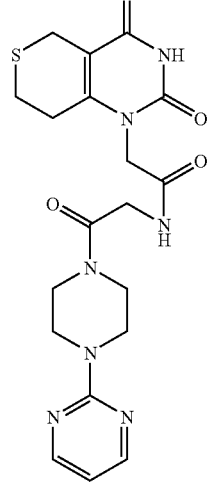 | 2.27 (B) | 446.1 |

-continued
| No. | Structure | Retention time $R_t$ [min] (HPLC method) | Mass [M + H]⁺ |
|---|---|---|---|
| 156 | 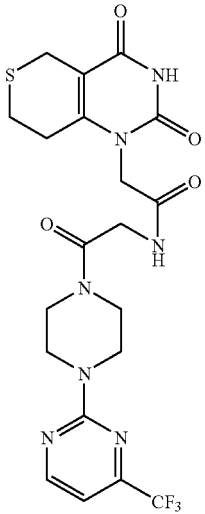 | 3.31 (B) | 514.2 |
| 157 | 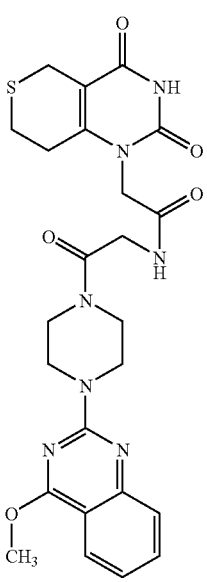 | 2.28 (B) | 526.1 |

-continued

| No. | Structure | Retention time R_t [min] (HPLC method) | Mass [M + H]+ |
|---|---|---|---|
| 158 | 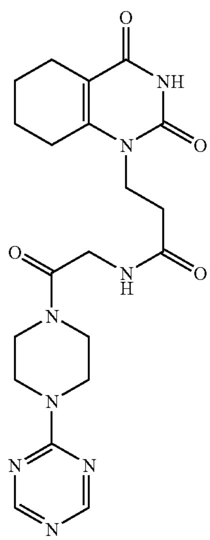 | 2.11 (B) | 443.2 |
| 159 | 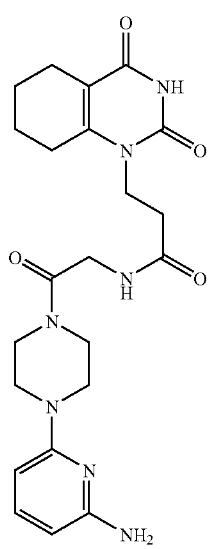 | 0.54 (B) | 456.2 |

-continued
| No. | Structure | Retention time $R_t$ [min] (HPLC method) | Mass $[M + H]^+$ |
|---|---|---|---|
| 160 | 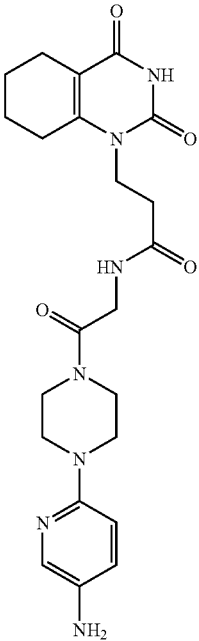 | 2.94 (A) | 456 |
| 161 | 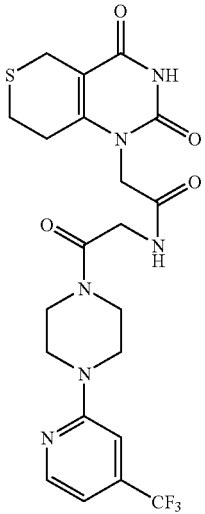 | 3.18 (B) | 513.1 |

-continued
| No. | Structure | Retention time $R_t$ [min] (HPLC method) | Mass [M + H]+ |
|---|---|---|---|
| 162 | 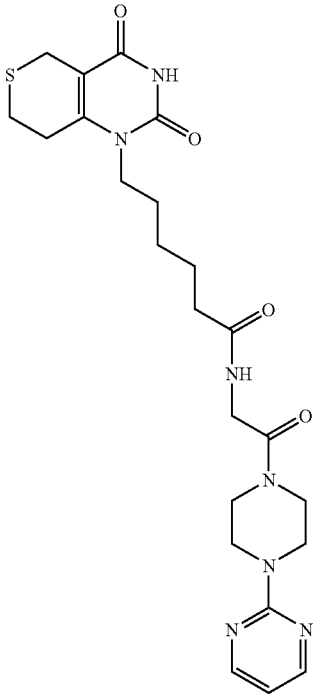 | 2.68 (B) | 502.1 |
| 163 | 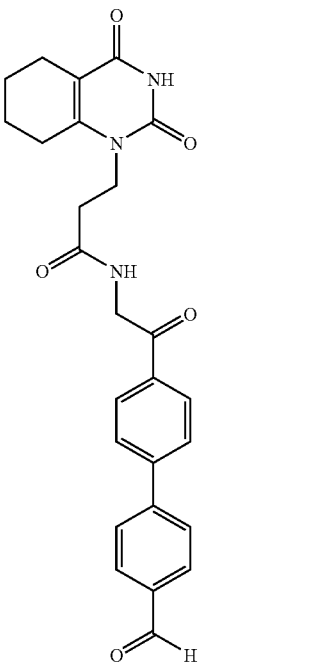 | 3.94 (A) | 460 |

-continued
| No. | Structure | Retention time R_t [min] (HPLC method) | Mass [M + H]+ |
|---|---|---|---|
| 164 | 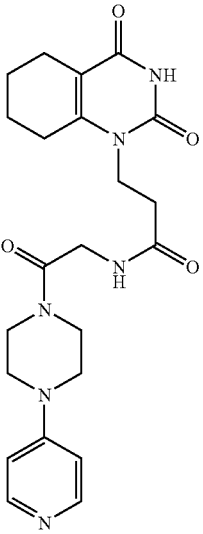 | 3.05 (A) | 441.3 |
| 165 | 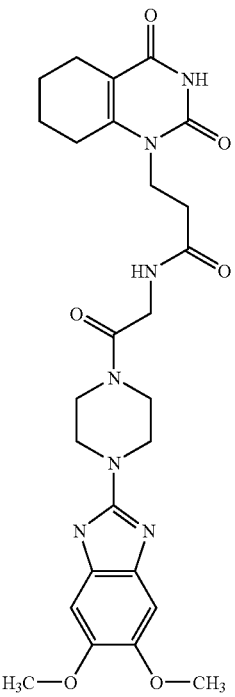 | 3.35 (A) | 540 |

-continued

| No. | Structure | Retention time R_t [min] (HPLC method) | Mass [M + H]+ |
|---|---|---|---|
| 166 | 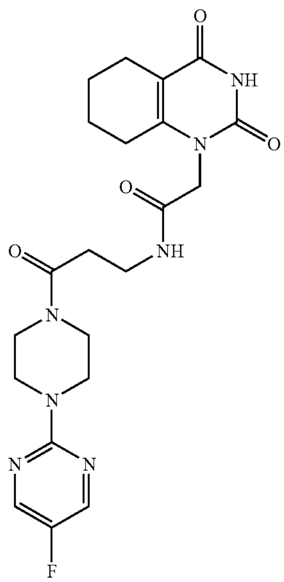 | 3.50 (A) | 460 |
| 167 | 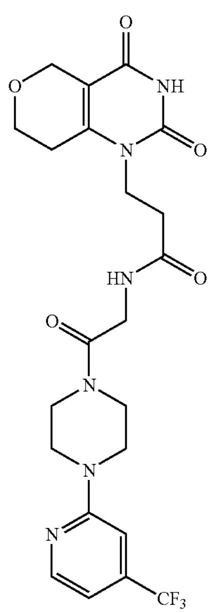 | 3.01 (B) | 511.2 |

| No. | Structure | Retention time $R_t$ [min] (HPLC method) | Mass $[M + H]^+$ |
|---|---|---|---|
| 168 | 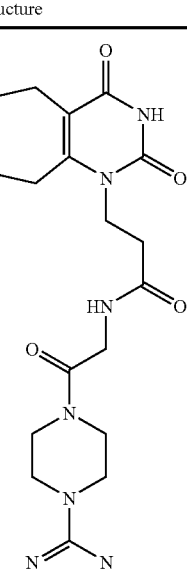 | 3.45 (B) | 524.1 |

HPLC Methods:

(A): Mobile phase A: 0.5% $HClO_4$ in water; mobile phase B: acetonitrile; gradient: 0.5 min. 98% A, 2% B; 4.5 min. 10% A, 90% B; 6.7 min. 98% A, 2% B; flow rate: 0.75 ml/min; column temperature: 30° C.; UV detection at 210 nm; column: Kromasil C18 (60×2 mm).

(B): Mobile phase A: 0.1% formic acid in water; mobile phase B: 0.1% formic acid in acetonitrile; gradient: 0 min. 90% A, 10% B; 4 min. 10% A, 90% B; 6.1 min. 90% A, 10% B; flow rate: 0.5 ml/min; column temperature: 40° C.; UV detection at 210 nm; column: Symmetry C18 (50×2.1 mm).

(C): Mobile phase A: 0.06% HCl in water; mobile phase B: acetonitrile; gradient: 1 min. 90% A, 10% B; flow rate: 0.6 ml/min; 4 min. 10% A, 90% B; flow rate: 0.8 ml/min; column temperature: 50° C.; UV detection at 210 nm; column: Symmetry C18 (150×2.1 mm).

The invention claimed is:

1. A compound of the formula (I)

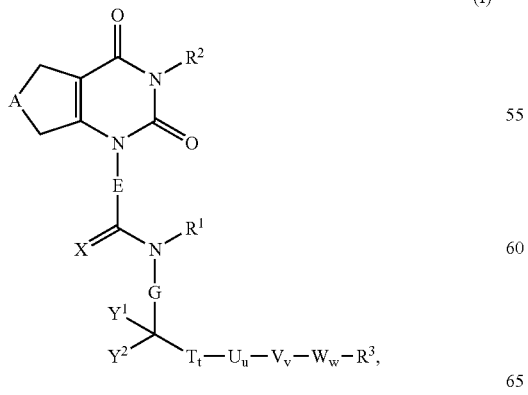

(I)

in which

A is a ring member selected from the group of:

—$CH_2$-D-, resulting in a fused 6-membered ring which contains D and includes the double bond shown in formula (I), wherein when D is a heteroatom, D is located in the 4-position relative to the nitrogen atom which is bonded to said 6-membered ring, and -D-$CH_2$—, resulting in a fused 6-membered ring which contains D and includes the double bond shown in formula (I), wherein when D is a heteroatom, D is located in the 3-position relative to the nitrogen atom which is bonded to said 6-membered ring,

—$CH_2CH_2CH_2$—;

in which

D represents —$CH_2$—, —O— or —S—,

E represents $(C_1-C_6)$-alkylene or $(C_3-C_8)$-cycloalkylene which are optionally mono- or polysubstituted, independently of one another, by substituents selected from the group of $(C_1-C_4)$-alkoxy, hydroxyl and amino, G represents $(C_1-C_6)$-alkylene or $(C_3-C_8)$-cycloalkylene which are optionally mono- or polysubstituted, independently of one another, by substituents selected from the group of $(C_1-C_4)$-alkoxy, hydroxyl and amino, T represents a methylene group, t represents 0 or 1, U represents $(C_6-C_{10})$-arylene, 5- to 7-membered heterocyclene having up to three heteroatoms from the group N, O and S or represents ethinediyl, where the ring systems may be substituted up to three times, independently of one another, by substituents selected from the group of nitro, cyano, halogen, $(C_1-C_6)$-alkyl, $(C_3-C_8)$-cycloalkyl, $(C_1-C_6)$-alkoxy, trifluoromethyl, di- and trifluoromethoxy, hydroxyl, amino, mono- and di-$(C_1-C_6)$-alkylamino, $(C_1-C_6)$-alkoxy-carbonyl, aminosulphonyl, $(C_1-C_6)$-alkylsulphonyl, mono- and di-$(C_1-C_6)$-alkylaminosulphonyl and $(C_1-C_6)$-alkanoyloxy, u represents 0 or 1, V represents $(C_6-C_{10})$-arylene, 5-, to 7-membered heterocyclene having up to three heteroatoms from the group N, O and S or represents ethinediyl, where the ring systems may be substituted up to three times, independently of one another, by substituents selected from the group of nitro, cyano, halogen, $(C_1-C_6)$-alkyl, $(C_3-C_8)$-cycloalkyl, $C_1-C_6$-alkoxy, trifluoromethyl, di- and trifluoromethoxy, hydroxyl, amino, mono- and di-$(C_1-C_6)$-alkylamino, $(C_1-C_6)$-alkoxy-carbonyl, aminosulphonyl, $(C_1-C_6)$-alkylsulphonyl, mono- and di-$(C_1-C_6)$-alkylaminosulphonyl and $(C_1-C_6)$-alkanoyloxy, v represents 0 or 1, W represents —O—, —S—, —CO—O—, —O—CO— or —NR$^4$—, in which R$^4$ represents hydrogen or $(C_1-C_6)$-alkyl, w represents 0 or 1, X represents O, S or N—R$^5$, in which R$^5$ represents hydrogen, $(C_1-C_6)$-alkyl or benzyl, Y$^1$ represents hydrogen, Y$^2$ represents hydroxyl, or Y$^1$ and Y$^2$ together represent O, S or N—R$^6$, in which R$^6$ represents hydrogen, $(C_1-C_6)$-alkyl or benzyl, R$^1$ represents hydrogen, $(C_1-C_6)$-alkyl which may be mono- or polysubstituted by halogen, or represents $(C_3-C_8)$-cycloalkyl, R$^2$ represents hydrogen or $(C_1-C_6)$-alkoxycarbonyl, and R$^3$ represents $(C_6-C_{10})$-aryl or a 5- to 13-membered heterocycle having up to four heteroatoms from the group N, O and S, where the ring systems may be substituted up to three times, independently of one another, by substituents selected from the group of nitro, cyano, halogen, $(C_1-C_6)$-alkyl, $(C_3-C_8)$-cycloalkyl, $(C_1-C_6)$-alkoxy, trifluoromethyl, di- and trifluoromethoxy, hydroxyl, oxo, amino, mono- and di-$(C_1-C_6)$-alkylamino, mono- and di-$(C_1-C_6)$-alkylaminomethyl, $(C_1-C_6)$-alkoxycarbonyl, aminosulphonyl, $(C_1-C_6)$-alkylsulphonyl, mono- and di-$(C_1-C_6)$-alkylaminosulphonyl, $(C_1-C_6)$-alkanoyl, $(C_1-C_6)$-alkanoyloxy and —CH$_2$—R$^7$, in which R$^7$ represents a 5- to 7-membered heterocycle having up to three heteroatoms from the group N, O and S, or a pharmaceutically acceptable salt thereof.

2. A compound according to claim 1, in which

A represents a ring member —CH$_2$-D- or -D-CH$_2$—, in which

D represents —CH$_2$—, —O— or —S—,

E represents $(C_1-C_6)$-alkylene which is optionally mono- or polysubstituted, independently of one another, by substituents selected from the group of $(C_1-C_4)$-alkoxy, hydroxyl and amino, G represents $(C_1-C_4)$-alkylene which is optionally mono- or polysubstituted, independently of one another, by substituents selected from the group of $(C-C_4)$-alkoxy, hydroxyl and amino, t represents 0, U represents phenylene, 6-membered heterocyclene having up to three heteroatoms from the group N, O and S, where the ring systems may be substituted up to three times, independently of one another, by substituents selected from the group of nitro, cyano, fluorine, chlorine, $(C_1-C_6)$-alkyl, $(C_3-C_3)$-cycloalkyl, $(C_1-C_6)$-alkoxy, trifluoromethyl, and di- and trifluoromethoxy, u represents 0 or 1, V represents phenylene, 6-membered heterocyclene having up to three heteroatoms from the group N, O and S, where the ring systems may be substituted up to three times, independently of one another, by substituents selected from the group of nitro, cyano, fluorine, chlorine, $(C_1-C_6)$-alkyl, $(C_3-C_6)$-cycloalkyl, $(C_1-C_6)$-alkoxy, trifluoromethyl, and di- and trifluoromethoxy, v represents 0 or 1, W represents —O—, —S—, —CO—O—, —O—CO— or —NR$^4$—, in which R$^4$ represents hydrogen or $(C_1-C_6)$-alkyl, w represents 0 or 1, X represents O, Y$^1$ represents hydrogen, Y$^2$ represents hydroxyl, or Y$^1$ and Y$^2$ together represent O, R$^1$ represents hydrogen or $(C_1-C_6)$-alkyl which may be mono- or poly-substituted by halogen, R$^2$ represents hydrogen, and R$^3$ represents phenyl, naphthyl or a 5- to 1 0-membered heterocycle having up to four heteroatoms from the group N, O and S, where the ring systems may be substituted up to three times, independently of one another, by substituents selected from the group of nitro, cyano, halogen, $(C_1-C_6)$-alkyl, $(C_3-C_6)$-cycloalkyl, $(C_1-C_6)$-alkoxy, trifluoromethyl, di- and trifluoromethoxy, hydroxyl, oxo, amino, and mono- and di-$(C_1-C_6)$-alkylamino, or a pharmaceutically acceptable salt thereof.

3. A compound according to claim 1, in which

A represents a ring member —CH$_2$-D- or -D-CH$_2$—, in which

D represents —CH$_2$— or —S—,

E represents a methylene or 1,2-ethylene group,

G represents a methylene or 1,2-ethylene group, t represents 0,

U represents phenylene, pyridinediyl or piperazine-1,4-diyl, u represents 0 or 1, V represents pyrimidinyl, v represents 0 or 1, W represents —O—, —CO—O— or —O—CO—, w represents 0 or 1, X represents O, $Y^1$ and $Y^2$ together represent O, $R^1$ represents hydrogen, $R^2$ represents hydrogen, and $R^3$ represents phenyl, napthbyl, thienyl, pyridyl, pyrazinyl, pyrimidinyl, thienopyrimidinyl, isoxazolyl, 1,3-benzodioxolyl or pyrrolidinyl, where the ring systems may in each case be substituted up to two times, independently of one another, by substituents selected from the group of nitro, cyano, bromine, chlorine fluorine, hydroxyl, ($C_1$–$C_3$)-alkoxy, ($C_1$–$C_3$)-alkyl, ($C_3$–$C_6$)-cycloalkyl, trifluoromethyl, amino and di-($C_1$–$C_3$)-alkylamino, or a pharmaceutically acceptable salt thereof.

4. A compound chosen from the group consisting of

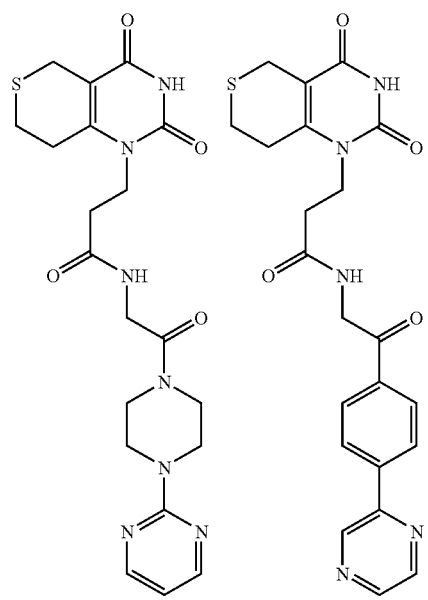

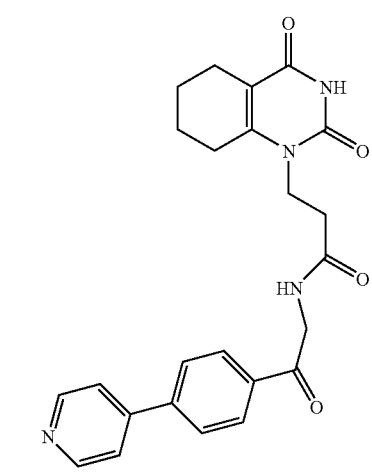

-continued

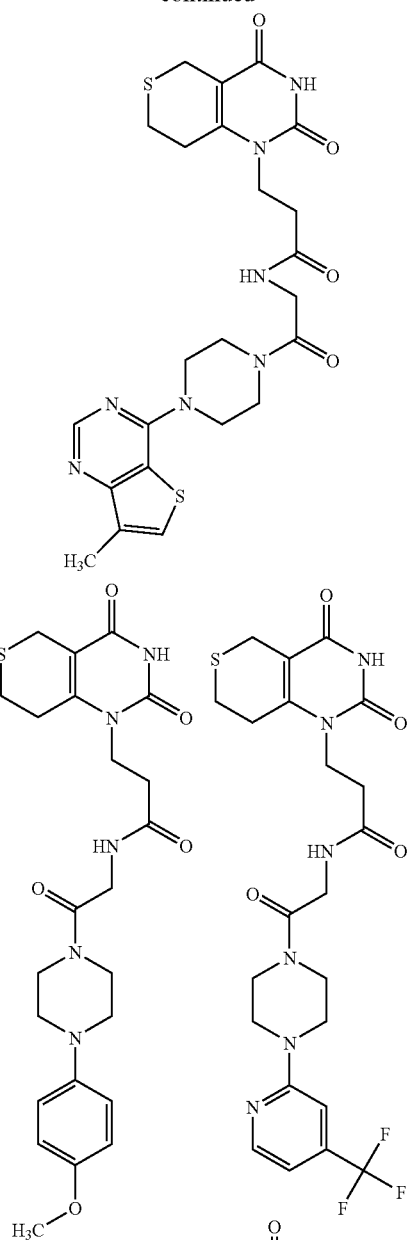

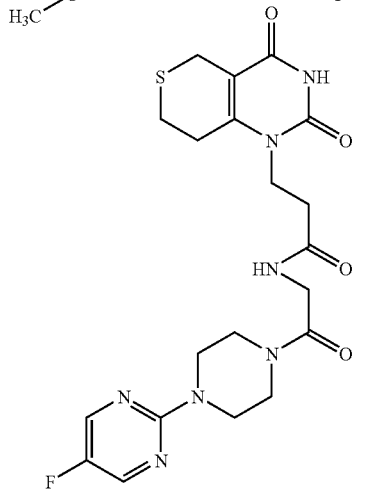

-continued

[Structure: thiopyrano-pyrimidinedione with propanamide linker to piperazinyl-pyridine]

and

[Structure: thiopyrano-pyrimidinedione with acetamide linker to piperazinyl-(5-fluoropyrimidine)]

or a pharmaceutically acceptable salt thereof.

5. A pharmaceutical composition, comprising at least one compound of the formula (I), as defined in claim 1, and at least one further active compound.

6. A pharmaceutical composition, comprising at least one compound of the formula (I), as defined in claim 1, and at least one further auxiliary.

7. A method for treatment of ischaemia or reperfusion damage, comprising administering an effective amount of a compound of formula (I), as defined in claim 1.

8. A process for preparing compounds of the formula (I), as defined in claim 1, comprising
reacting a compound of the formula (IV)

(IV)

[Structure IV]

in which
Z represents an alkyl or benzyl radical and A, E and X are as defined in claim 1,
with chlorocarbonyl isocyanate to give a compound of the formula (V)

(V)

[Structure V]

in which
Z represents an alkyl or benzyl radical and A, S and X are as defined in claim 1, converting the resulting reaction product, in a subsequent step, into a compound of the formula (VI), (VI)

[Structure VI]

in which
A, E and X are as defined in claim 1,
and then this is
either
[A] convened using a compound of the formula (VII)

(VII)

[Structure VII]

in which G, $R^1$, $R^3$, T, U, V, W, $Y^1$, $Y^2$, t, u, v and w are as defined in claim 1
into a compound of the formula (VIII)

(VIII)

[Structure VIII]

in which A, E, G, $R^1$, $R^3$, T, U, V, W, X, $Y^1$, $Y^2$, t, u, v and w are as defined in claim 1,
or
[B] converted using a compound of the formula (VIIa), (VIIa)

[Structure VIIa]

in which G $R^1$, T, U, V, $Y^1$, $Y^2$, t and u are as defined in claim 1, v is 1, w is 0 and V contains as an additional substituent a suitable leaving group,
via the stage of a compound of the formula (VIIIa),

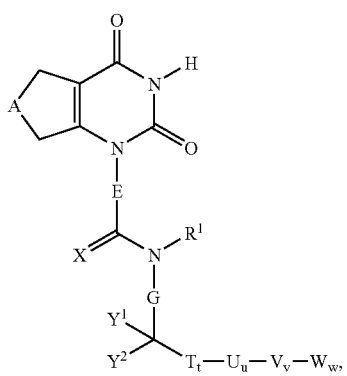

(VIIIa)

in which A, E, G, $R^1$, T, U, V, X, $Y^1$, $Y^2$ t and u are as defined in claim 1, v is 1, w is 0 and V contains as an additional substituent a suitable leaving group, and a subsequent aryl coupling reaction in the presence of a catalyst with a compound of the formula (IX)

$R^3$-M          (IX)

in which
  $R^3$ is as defined in claim 1 and M is an optionally substituted metallic or semimetallic element,
into a compound of the formula (VIII)
and the compound of the formula (VIII) is, if appropriate, reacted with a compound of the formula (X)

$R^2$-Q          (X)

in which
  $R^2$ is as defined in claim 1, but not hydrogen, and Q represents a leaving group,
to give a compound of the formula (I) in which $R^2$ is as defined in claim 1, but not hydrogen.

9. A process for preparing compounds of the formula (I), as defined in claim 1, comprising
converting a compound of the formula (VI)

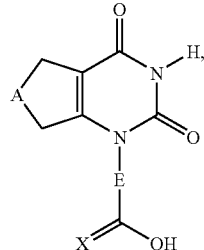

(VI)

in which
  A, E and X are as defined in claim 1,
[A] with a compound of the formula (VII)

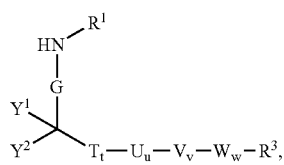

(VII)

in which G, $R^1$, $R^3$, T, U, V, W, $Y^1$, $Y^2$, t u, v and w are as defined in claim 1
into a compound of the formula (VIII)

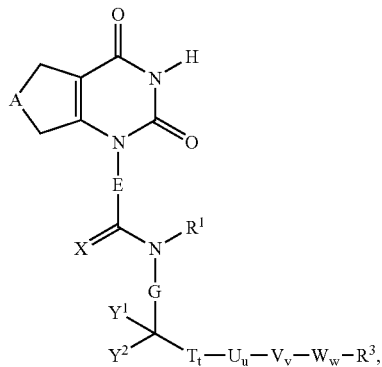

(VIII)

in which A, E, G, $R^1$, $R^3$, T, U, V, W, X, $Y^1$, $Y^2$, t, u, v and w are as defined in claim 1,
or
[B] with a compound of the formula (VIIa)

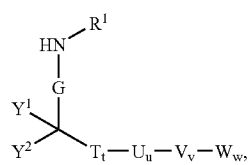

(VIIa)

in which G, $R^1$, T, U, V, $Y^1$, $Y^2$, t and u are as defined in claim 1, v is 1, w is 0 and V contains as an additional substituent a suitable leaving group,
via the stage of a compound of the formula (VIIIa)

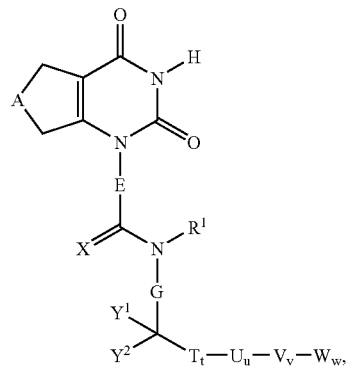

(VIIIa)

in which A, E, G, $R^1$, T, U, V, X, $Y^1$, $Y^2$, t and u are as defined in claim 1, v is 1, w is 0 and V contains as an additional substituent a suitable leaving group,
and subsequent aryl coupling reaction in the presence of a catalyst with a compound of the formula (IX)

$R^3$-M          (IX)

in which
  $R^3$ is as defined in claim 1 and M is an optionally substituted metallic or semimetallic element,
into a compound of the formula (VIII)

and, if appropriate, converting the compound of the formula (VIII) with a compound of the formula (X)

$$R^2\text{-}Q \tag{X}$$

in which

R² is as defined in claim 1, but not hydrogen, and Q represents a leaving group, into a compound of the formula (I) in which R² is as defined in claim 1, but not hydrogen.

10. The process of claim 8, wherein in the definition of R³, M is zinc, magnesium, boron, lithium, copper or tin.

11. The process of claim 9, wherein in the definition of R³, M is zinc, magnesium, boron, lithium, copper or tin.

* * * * *